United States Patent
Kim et al.

(10) Patent No.: US 11,034,773 B2
(45) Date of Patent: *Jun. 15, 2021

(54) METHODS AND MATERIALS FOR TREATING CANCER

(71) Applicant: Mayo Foundation for Medical Education and Research, Rochester, MN (US)

(72) Inventors: Yon Son Betty Kim, Jacksonville Beach, FL (US); Robert E. Wharen, Jr., Jacksonville, FL (US); Hengfeng Yuan, Shanghai (CN); Wen Jiang, Houston, TX (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 14 days.

This patent is subject to a terminal disclaimer.

(21) Appl. No.: 16/726,571

(22) Filed: Dec. 24, 2019

(65) Prior Publication Data

US 2020/0216561 A1 Jul. 9, 2020

Related U.S. Application Data

(62) Division of application No. 15/417,721, filed on Jan. 27, 2017, now Pat. No. 10,556,965.

(Continued)

(51) Int. Cl.
*C07K 16/32* (2006.01)
*A61K 9/51* (2006.01)

(Continued)

(52) U.S. Cl.
CPC ............. *C07K 16/32* (2013.01); *A61K 9/51* (2013.01); *A61K 38/1738* (2013.01);
(Continued)

(58) Field of Classification Search
CPC ............. C07K 16/32; C07K 16/2866; C07K 2317/23; A61K 9/51; A61K 47/6933; A61K 38/1738; A61K 2039/507
See application file for complete search history.

(56) References Cited

U.S. PATENT DOCUMENTS

| 6,518,397 B1 | 2/2003 | Dedhar |
| 7,488,711 B2 | 2/2009 | Tosato et al. |

(Continued)

FOREIGN PATENT DOCUMENTS

| CN | 103735514 | 4/2014 |
| WO | WO 2008032153 | 3/2008 |

OTHER PUBLICATIONS

Doug et al., "Induction of protective immunity against mycobacterium tuberculosis by delivery of ESX antigens into airway dendritic cells," Mucosal Immunology, May 2013, 6(3):522-534.

(Continued)

*Primary Examiner* — Trevor Love
(74) *Attorney, Agent, or Firm* — Fish & Richardson P.C.

(57) ABSTRACT

This document provides methods and materials related to treating cancer. For example, methods and materials for using particles (e.g., nanoparticles) containing (a) one or more molecules having the ability to bind to a cancer cell (e.g., a human breast cancer cell) and (b) one or more molecules having the ability to bind to an APC (e.g., a human macrophage) to treat cancer are provided.

4 Claims, 33 Drawing Sheets

Related U.S. Application Data

(60) Provisional application No. 62/288,329, filed on Jan. 28, 2016.

(51) Int. Cl.
   *C07K 16/28* (2006.01)
   *A61K 47/69* (2017.01)
   *A61K 38/17* (2006.01)
   *A61K 39/00* (2006.01)

(52) U.S. Cl.
   CPC ...... *A61K 47/6933* (2017.08); *C07K 16/2866* (2013.01); *A61K 2039/507* (2013.01); *C07K 2317/73* (2013.01)

(56) References Cited

U.S. PATENT DOCUMENTS

| | | |
|---|---|---|
| 9,095,568 B2 | 8/2015 | Berninger et al. |
| 9,527,906 B2 | 12/2016 | Gelfand et al. |
| 10,556,965 B2 | 2/2020 | Kim et al. |
| 2003/0113332 A1 | 6/2003 | Mathew et al. |
| 2005/0008649 A1 | 1/2005 | Shin et al. |
| 2006/0093612 A1 | 5/2006 | Srivastava |
| 2013/0121918 A1 | 5/2013 | Hong et al. |
| 2013/0121958 A1 | 5/2013 | Leclerc et al. |
| 2014/0271683 A1 | 9/2014 | Chao et al. |
| 2017/0218086 A1 | 8/2017 | Kim et al. |

OTHER PUBLICATIONS

Lehmann et al., "Direct Delivery of Antigens to Dendritic Cells via Antibodies Specific for Endocytic Receptors as a Promising Strategy for Future Therapies," Vaccines, Jun. 2016, 4(2):8, 32 pages.

Pazina et al., "The anti-SLAMF7 antibody elotuzumab mediates NK cell activation through both CD16-dependent and -independent mechanisms," Oncoimmunology, Jun. 2017, 6(9):e1339853.

Velmurugan et al., "Phagocytosis of antibody-opsonized tumor cells leads to the formation of a discrete vacuolar compartment in macrophages," Traffic, Apr. 2018, 19(4):273-284.

Basu et al., "CD91 is a common receptor for heat shock proteins gp96, hsp90, hsp70, and calreticulin," Immunity., 14(3):303-313, Mar. 2001.

Cavallo, Blocking CD47 Signals May Offer New Therapeutic Approach in the Treatment of Pancreatic Cancer, 2014, ascopost, http://www.ascopost.corn/News/16233, pp. 1-4. (Year: 2014).

Chao et al, "Calreticulin is the dominant pro-phagocytic signal on multiple human cancers and is counterbalanced by CD47," Sci. Transl. Med., 2(63):1-21, Dec. 2010.

Chen et al., "SLAMF7 is critical for phagocytosis of haematopoietic tumour cells via Mac-1 integrin," Nature, 544(7651):493-497, Apr. 2017.

Dominguez and Lustgarten, "Targeting the tumor microenvironment with anti-neu/anti-CD40 conjugated nanoparticles for the induction of antitumor immune responses," Vaccine., 28(5):1383-1390, Feb. 3, 2010.

Fadeel et al, "Buried alive: a novel approach to cancer treatment," FASEB J., 18(1):1-4, Jan. 2004.

Gogishvili et al., "SLAMF7-CAR T cells eliminate myeloma and confer selective fratricide of SLAMF7+ normal lymphocytes," Blood, 130(26):2838-2847, Dec. 2017.

Jenkins et al., "Mechanisms of resistance to immune checkpoint inhibitors," Br. J. Cancer, 118(1):9-16, Jan. 2018.

Jiang et al., "Design and characterization of lysine cross-linked mercapto-acid biocompatible quantum dots," Chem Mater., 18(4):872-878, 2006.

Kang et al., "Enhancing Glioblastoma-Specific Penetration by Functionalization of Nanoparticles with an Iron-Mimic Peptide Targeting Transferrin/Transferrin Receptor Complex," Mol Pharmaceutics., 12(8):2947-2961, 2015.

Klarquist and Janssen, "Melanoma-infiltrating dendritic cells. Limitations and opportunities of mouse models," Oncoimmunology., 1(9):1584-1593, Dec. 1, 2012.

Kumaresan et al., "CS1, a novel member of the CD2 family, is homophilic and regulates NK cell function," Molecular immunology, 39(1-2):1-8, Sep. 2002.

Malaer and Mathew "CS1 (SLAMF7, CD319) is an effective immunotherapeutic target for multiple myeloma," American journal of cancer research, 7(8):1637, Aug. 2017.

Mosser and Zhang., "Activation of Murine Macrophages," Curr Protoc Immunol., 83:14.2.1-14.2.8, Nov. 1, 2008.

Obeid et al., "Calreticulin exposure dictates the immunogenicity of cancer cell death," Nat Med., 13(1):54-61, Jan. 2007.

Qie et al., "Surface modification of nanoparticles enables selective evasion of phagocytic clearance by distinct macrophage phenotypes," Sci Rep., 6:26269, May 19, 2016.

Shao et al, Nanoparticle-Based Immunotherapy for Cancer, 2015, ACSNANO, vol. 9, No. 1, pp. 16-30. (Year: 2015).

Stephan and Irvine, "Enhancing cell therapies from the outside in: Cell surface engineering using synthetic nanomaterials," Nanotoday., 6(3):309-325, Jun. 1, 2011.

Weiskopf et al., "Engineered SIRP a Variants as Immunotherapeutic Adjuvants to Anticancer Antibodies," Science., 341(6141):88-91, Jul. 5, 2013.

Wu et al., "Whole-cell vaccine coated with recombinant calreticulin enhances activation of dendritic cells and induces tumour-specific immune responses," Oncology Reports., 29(2):529-534, Feb. 2013.

Yuan et al., "Multivalent Bi-Specific Nano-Bioconjugate Engager for Targeted Cancer Immunotherapy," Nat Nanotechnol., 12(8):763-769, Aug. 2017.

Zhang et al., "Combating HER2-overexpressing breast cancer through induction of calrecticulin exposure by Tras-Permut CrossMab," Oncoimmunology., 4(3):e994391, Mar. 2015, 13 pages.

| Sample | Schematic | Hydrodynamic diameter (nm) | Zeta potential (mv) |
|---|---|---|---|
| NP alone | | 32.6±1.1 | -28.5±0.8 |
| HER2-NP | | 49.6±1.3 | -24.1±1.7 |
| CRT-NP | | 40.4±0.9 | -25.6±1.4 |
| mBiNE* | | 45.3±1.6 | -24.9±1.5 |

*anti-HER2 antibody:CRT = 1:1

*Abbreviation: NP, nanoparticle; CRT, calreticulin; mBiNE, multivalent bi-specific (anti-HER2 antibody and calreticulin) nano-bioconjugate engager.*

Figure 16

METHODS AND MATERIALS FOR TREATING CANCER

CROSS-REFERENCE TO RELATED APPLICATIONS

This application is a divisional of U.S. application Ser. No. 15/417,721, filed Jan. 27, 2017 (now U.S. Pat. No. 10,556,965), which claims the benefit of U.S. Provisional Application Ser. No. 62/288,329, filed Jan. 28, 2016. The disclosure of the prior application is considered part of (and is incorporated by reference in) the disclosure of this application.

BACKGROUND

1. Technical Field

This document relates to methods and materials involved in treating cancer. For example, this document relates to methods and materials involved in using particles (e.g., nanoparticles) containing (a) one or more molecules having the ability to bind to a cancer cell (e.g., a human breast cancer cell) and (b) one or more molecules having the ability to bind to an antigen presenting cell (e.g., a human macrophage) to treat cancer.

2. Background Information

The innate immune system is integral to the host's defense against foreign pathogens and essential to mediate cellular homeostasis. The first lines of defense are the professional antigen presenting cells (APCs) of the innate immune system, the gatekeepers of the body's immune system. These cells are designed to detect and eradicate infected or diseased cells (via phagocytosis) within the body and process cellular components and proteins and present them as antigens to the adaptive immune system. The innate immune system alone, however, does not confer patient-specific or disease-specific clearance, nor does it have the ability to generate long-lasting immune memory. The memory and immune surveillance programs for the host are mediated by a more specialized and highly specific adaptive immune system involving T-cells.

SUMMARY

This document provides methods and materials involved in treating cancer. For example, this document provides methods and materials for using particles (e.g., nanoparticles) containing (a) one or more molecules having the ability to bind to a cancer cell (e.g., a human breast cancer cell) and (b) one or more molecules having the ability to bind to an APC (e.g., a human macrophage) to treat cancer. As described herein, particles (e.g., nanoparticles) can be designed to include a molecule having the ability to bind to a cancer cell such as an anti-cancer antigen antibody (e.g., anti-human epidermal growth factor receptor 2 (HER2) antibody) and a molecule having the ability to bind to an APC such as a calreticulin (CRT). Such particles can have the ability to facilitate the phagocytosis of cancer cells by APCs within a mammal's body and to activate down-stream adaptive immune responses (e.g., T cell responses) to treat cancer.

In general, one aspect of this document features a composition comprising, or consisting essentially of, particles, wherein the particles have a longest dimension of 1000 nm or less and comprise a molecule having the ability to bind to cancer cells and a molecule having the ability to bind to antigen presenting cells, wherein incubation of the cancer cells and the antigen presenting cells in the presence of the composition results in increased phagocytosis of the cancer cells by the antigen presenting cells as compared to the level of phagocytosis of comparable cancer cells by comparable antigen presenting cells in the absence of the composition. The longest dimension can be between 5 nm and 100 nm. The longest dimension can be between 10 nm and 50 nm. The longest dimension can be between 20 nm and 40 nm. The molecule having the ability to bind to cancer cells can be an anti-cancer antigen antibody. The anti-cancer antigen antibody can be an anti-CD340 antibody, an anti-EGFR antibody, or an anti-PSMA antibody. The molecule having the ability to bind to antigen presenting cells can be a polypeptide. The polypeptide can be a CRT polypeptide. The polypeptide can be a human CRT polypeptide. The cancer cells can be breast cancer cells, brain cancer cells, prostate cancer cells, lung cancer cells, or colorectal cancer cells. The cancer cells can be human breast cancer cells, human brain cancer cells, human prostate cancer cells, human lung cancer cells, or human colorectal cancer cells. The antigen presenting cells can be macrophages. The antigen presenting cells can be human macrophages. The increased phagocytosis can be at least a two-fold increase. The increased phagocytosis can be at least a four-fold increase.

In another aspect, this document features a method for treating a mammal having cancer. The method comprises, or consists essentially of, administering to the mammal a composition comprising, or consisting essentially of, particles, wherein the particles have a longest dimension of 1000 nm or less and comprise a molecule having the ability to bind to cancer cells and a molecule having the ability to bind to antigen presenting cells, wherein incubation of the cancer cells and the antigen presenting cells in the presence of the composition results in increased phagocytosis of the cancer cells by the antigen presenting cells as compared to the level of phagocytosis of comparable cancer cells by comparable antigen presenting cells in the absence of the composition. The longest dimension can be between 5 nm and 100 nm. The longest dimension can be between 10 nm and 50 nm. The longest dimension can be between 20 nm and 40 nm. The molecule having the ability to bind to cancer cells can be an anti-cancer antigen antibody. The anti-cancer antigen antibody can be an anti-CD340 antibody, an anti-EGFR antibody, or an anti-PSMA antibody. The molecule having the ability to bind to antigen presenting cells can be a polypeptide. The polypeptide can be a CRT polypeptide. The polypeptide can be a human CRT polypeptide. The cancer cells can be breast cancer cells, brain cancer cells, prostate cancer cells, lung cancer cells, or colorectal cancer cells. The cancer cells can be human breast cancer cells, human brain cancer cells, human prostate cancer cells, human lung cancer cells, or human colorectal cancer cells. The antigen presenting cells can be macrophages. The antigen presenting cells can be human macrophages. The increased phagocytosis can be at least a two-fold increase. The increased phagocytosis can be at least a four-fold increase. The mammal can be a human. The cancer can be breast cancer, brain cancer, prostate cancer, lung cancer, or colorectal cancer. The composition can be administered by injection, ingestion, or inhalation.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

Figure 10:
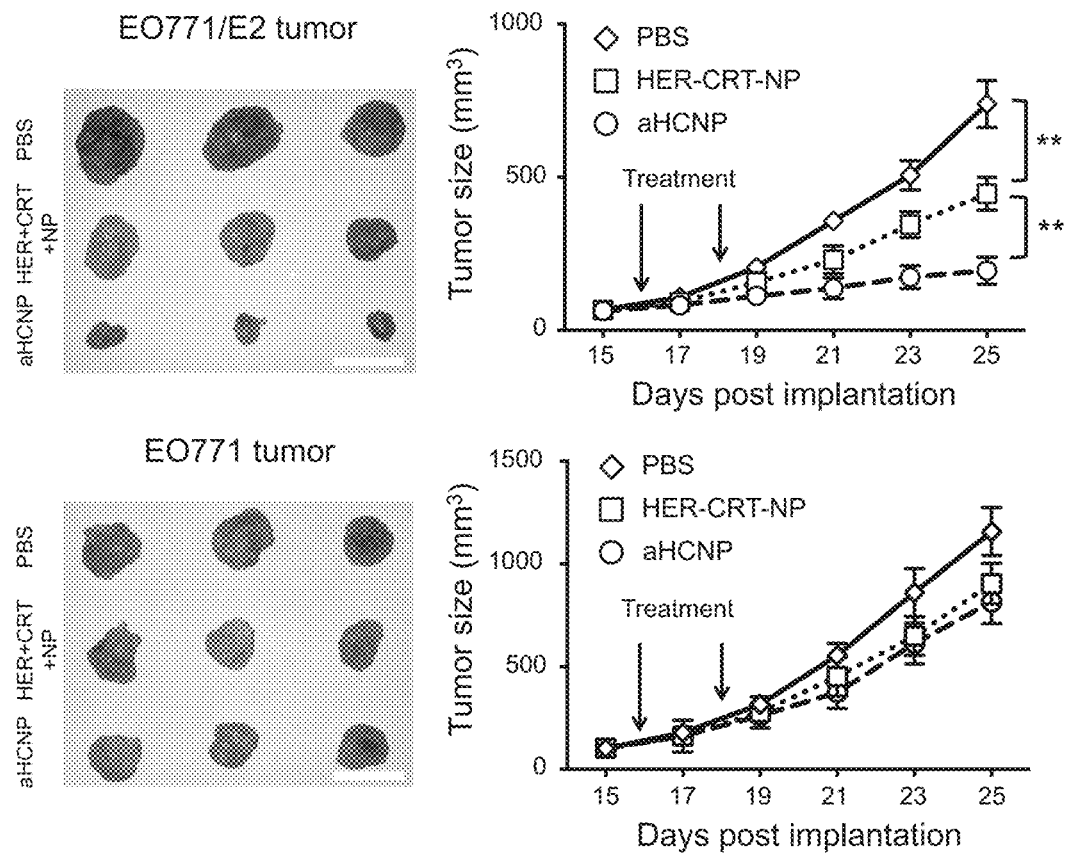

FIG. 10. aHCNP enable specific tumor growth inhibition. Treatments of aHCNP in both HER2 receptor over-expressing and HER2 receptor negative tumors showed that aHCNP selectively inhibited growth in EO771/E2 tumors significantly, while had minimal effect on HER2 negative EO771 tumors.

Figure 1:
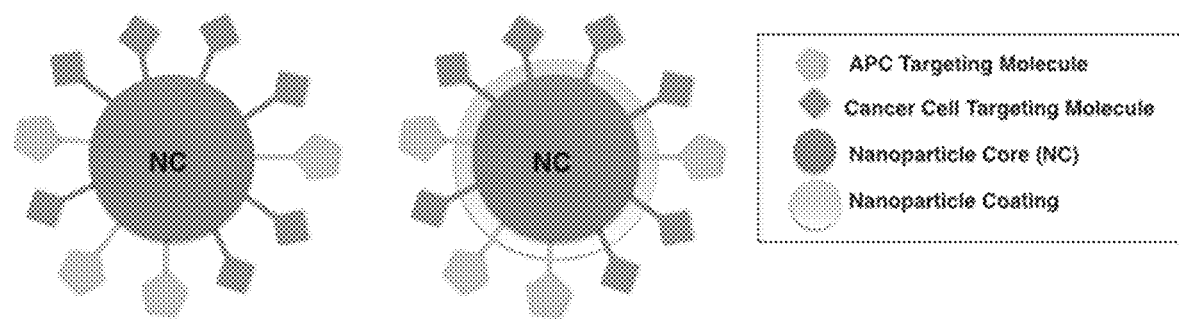
FIG. 1 is a diagram of two exemplary multivalent, bispecific nanoparticles. The nanoparticle material (e.g., metallic, semiconductor, polymer, and/or magnetic material) can be modified on its surface to include targeting biomolecules (e.g., DNA, RNA, polypeptide, and/or antibodies) so that the nanoparticle simultaneously recognizes biomolecules that are expressed (e.g., highly expressed) on cancer cells such as erB2 receptors (e.g., HER2) on cancer cells and APC membrane molecules on APCs. For example, anti-CD340 antibodies (squares) can be used to target erB2 receptors (e.g., HER2) on cancer cells, and CRT polypeptides (pentagons) can be used to target APCs. The ratio of these targeting biomolecules can be modulated during synthesis to achieve desired effects. In some cases, the nanoparticle can be modified by adding a coating layer to modulate the half-life of the nanoparticle within a mammal and to help the nanoparticle bypass the reticuloendothelial system.
Figure 2:
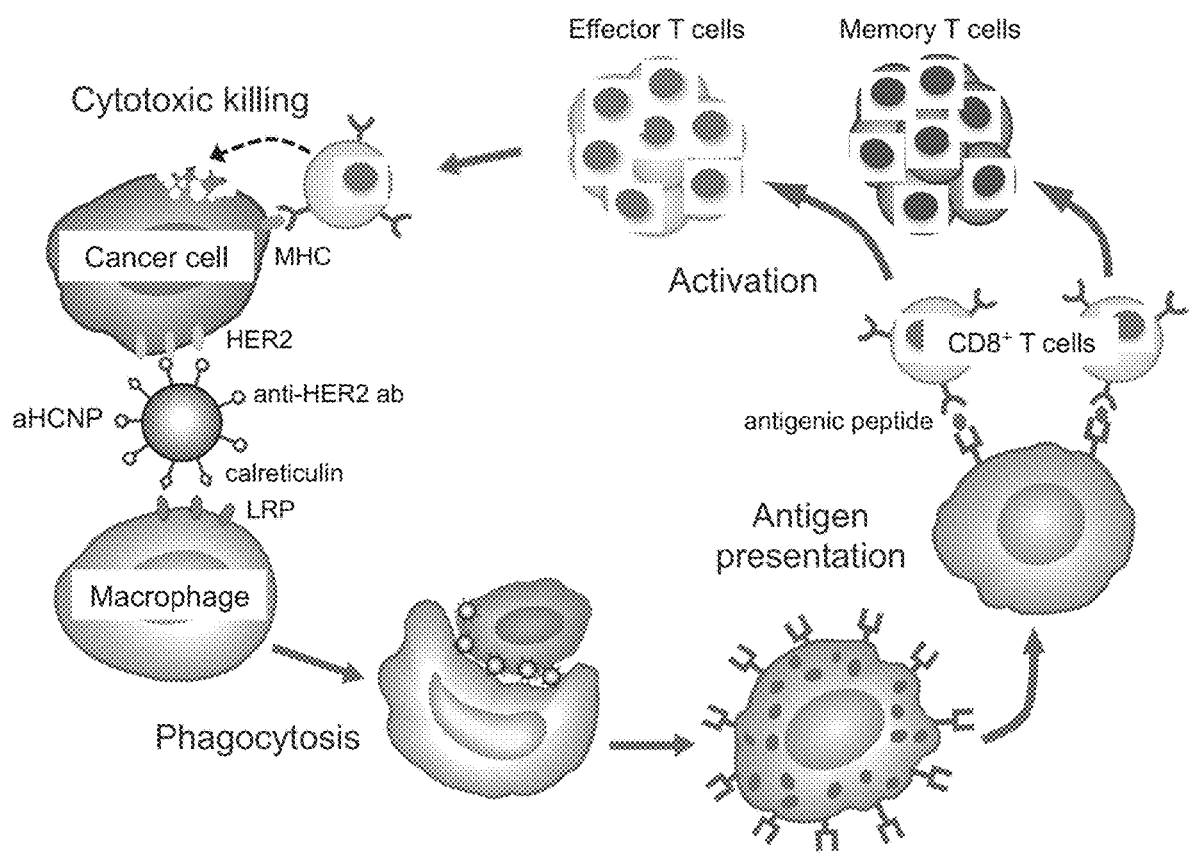
FIG. 2 is a diagram of a proposed mode of action for using nanoparticles provided herein to enhance both innate immune responses and acquired immune responses against cancer cells. For example, a functionalized nanoparticle (purple sphere) coated with an antibody that targets erB2 (HER2) receptor on cancer cell. The nanoparticle is also coated with a polypeptide called calreticulin that targets low-density lipoprotein receptor-related protein (LRP) receptors on antigen presenting cells such as macrophages. This serves as a linker that recruit macrophages to phagocytize the cancer cells that express the HER2 receptor, and subsequently resulting in the activation adaptive immune response. A sample multivalent bispecific nanoparticle is illustrated using anti-Herceptin/calreticulin nanoparticle bioconjugate (aHCNP). The four phases of (1) Nanoparticle recognition, between a diseased cancer cell and macrophages; (2) Nanoparticle-driven internationalization/phagocytosis of the cancer cell; (3) Tumor antigen presentation by the macrophage after engulfing the cancer cell; and (4) Activation of the adaptive immune system resulting in T cell activation for targeted cytotoxic cancer cell death and activation of the immune memory system.
Figures 1, 11:
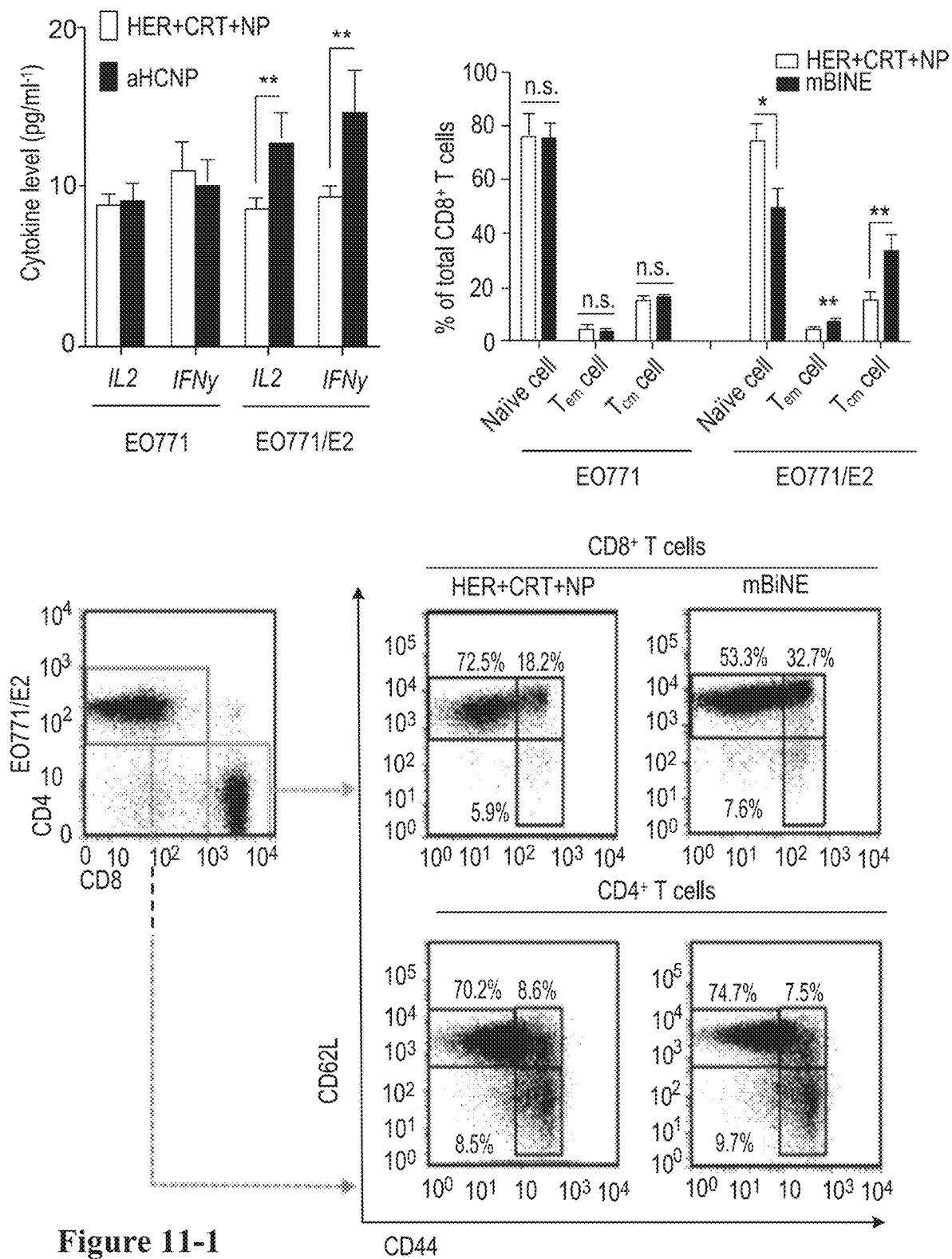
Figures 2, 11:
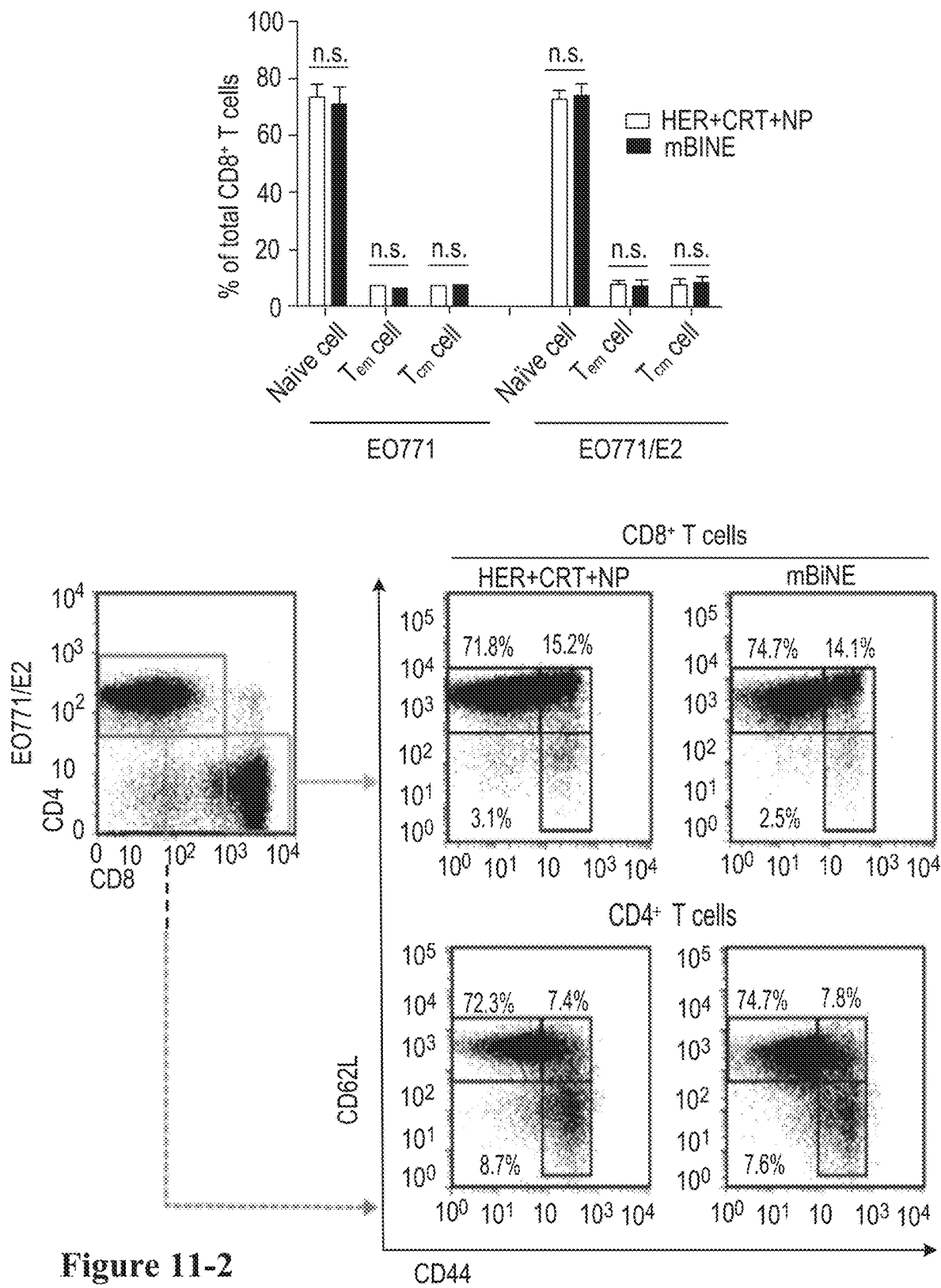

FIGS. 11-1 and 11-2. aHCNP treatments resulted in targeted increased systemic inflammatory cytokine production and CD8 T cell activation.

Figure 12:
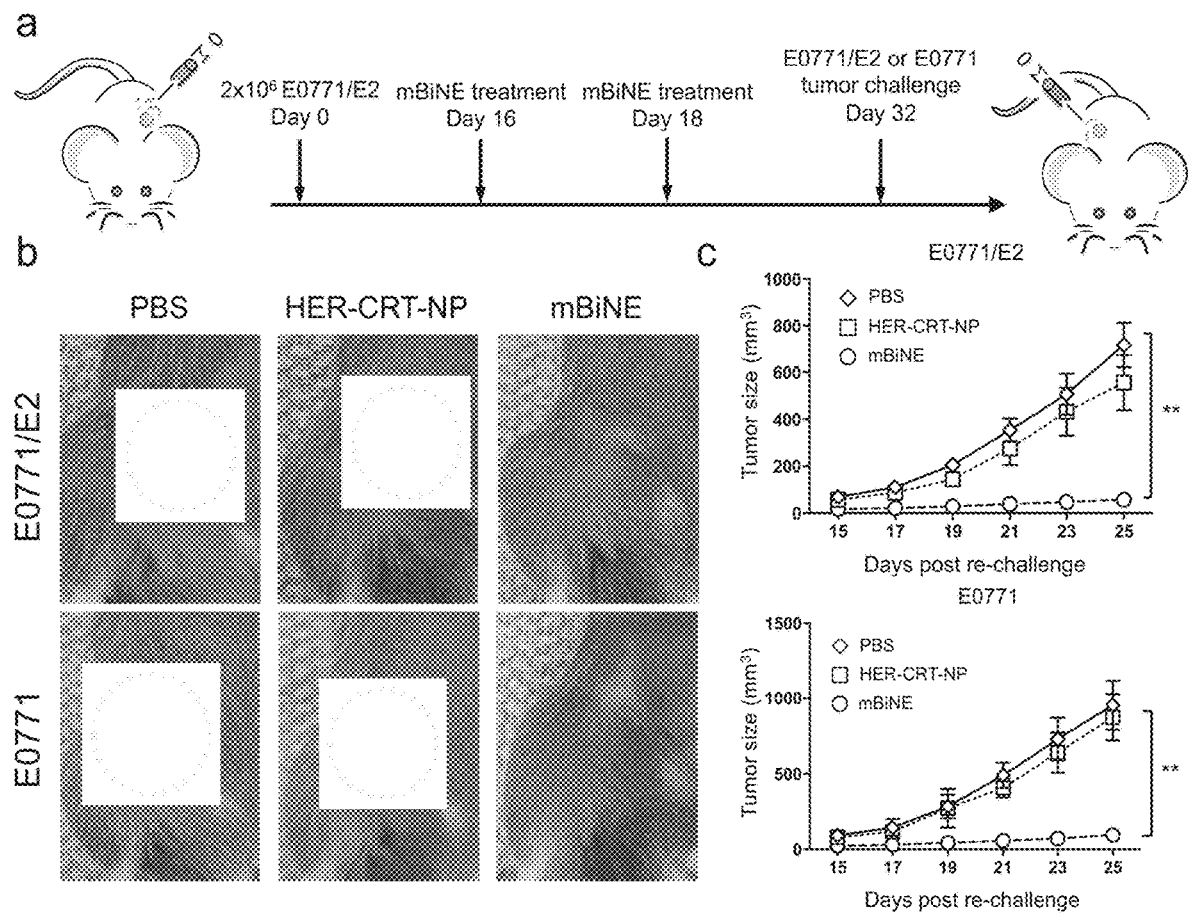

FIG. 12. aHCNP treatments result in the generation of long-term anti-tumor immune memory. (a) EO771/E2 tumors were initially implanted in the L mammary fat pad of the mice followed by treatment with PBS, conjugated HER-CRT-NP or aHCNP. This was followed by a second tumor re-challenge 2 weeks later, with implantation of either EO771 or EO771/E2 tumor into the mammary fat pad on the opposite side. (b-c) Both EO771 and EO771/E2 tumors failed to engraft in aHCNP treated mice, suggesting the establishment of anti-tumor immune memory against both HER2 positive and HER2 negative tumors.

Figure 13A:
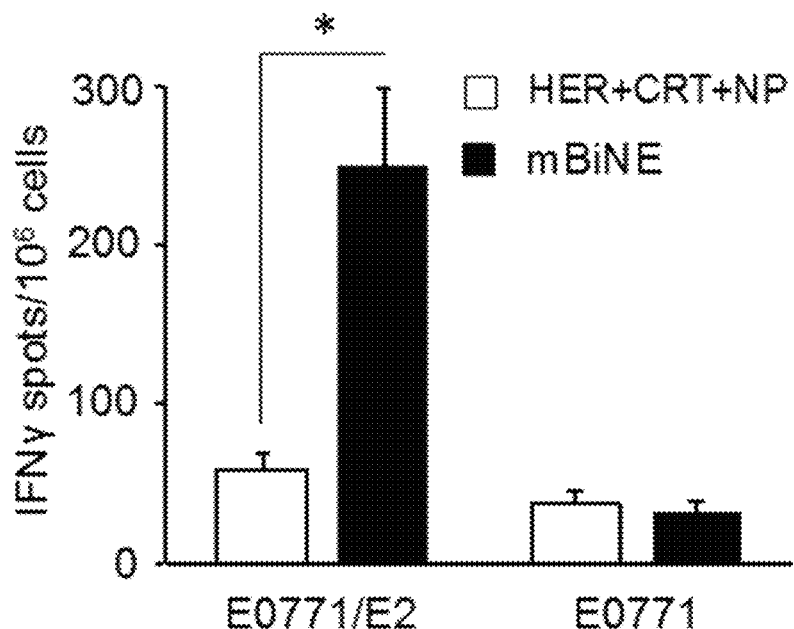

FIG. 13A. $CD8^+$ T cells from the draining lymph nodes of E0771 and E0771/E2 tumour bearing mice (n=5) were extracted 2 days after second dose of mBiNE treatment and re-stimulated with E0771 or E0771/E2 cells, respectively. IFN-γ-producing cells were assessed by ELISPOT assay.

Figure 13B:
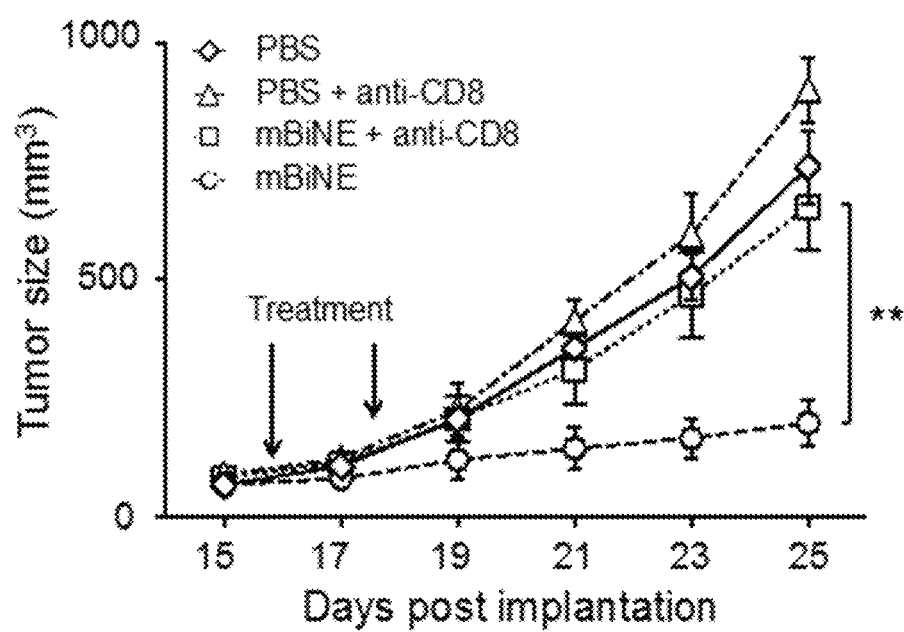

FIG. 13B. Depletion of CD8 T cells abrogated the anti-tumour effect of mBiNE in E0771/E2 tumour-bearing mice. For all graphs, data were presented as means±standard deviation. $*P<0.05$, $**P<0.01$. n.s.=not significant, by Mann-Whitney test for the indicated comparisons.

Figure 14:
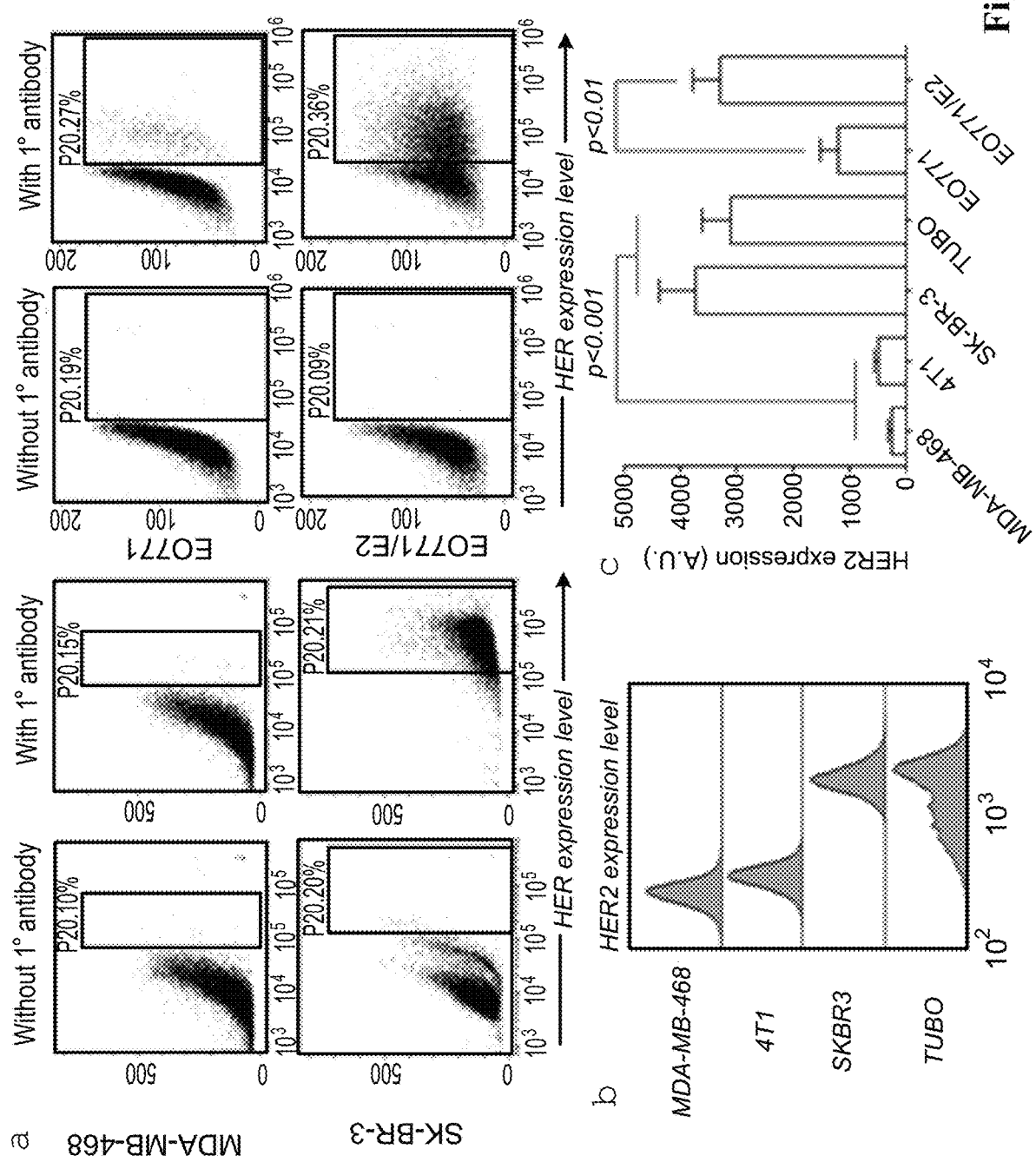

FIG. 14. HER2/neu expression analyses of both human and mouse mammary carcinoma cells. (A) Flow cytometry analyses of HER2 expressing levels in human SK-BR-3 and MDA-MB-468, and mouse E0771/E2 and E0771 cells. (B) HER2/neu expression analyses were also performed in mouse 4T1 and TUBO cells. (C) Quantified expression levels of HER2/neu in different cancer cell lines used in the study. Comparison was performed by Mann-Whitney test, error bars=mean±standard deviation, n=5.

Figure 15:
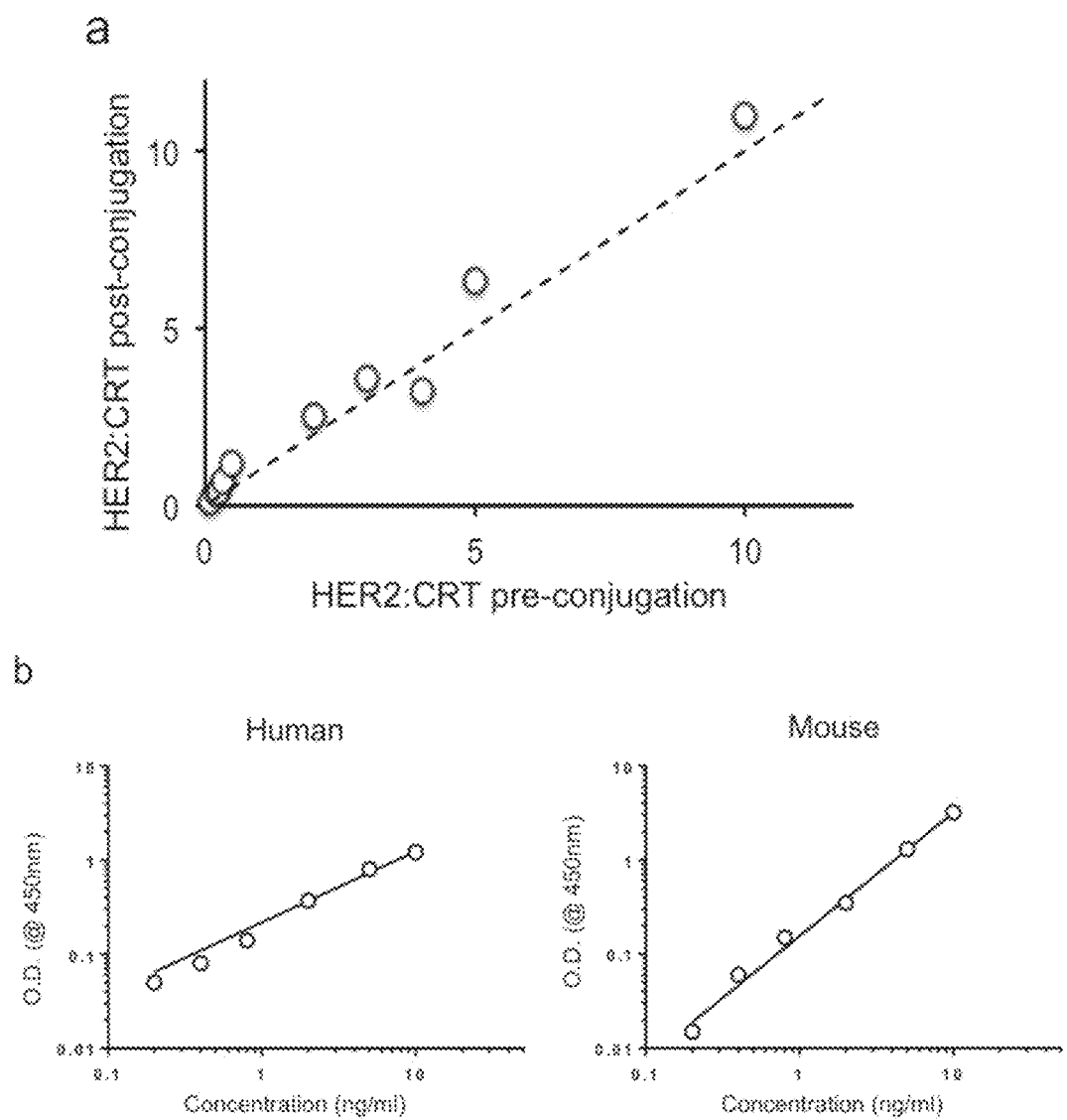

FIG. 15. Conjugation analysis for mBiNE. (A) The ratios of anti-HER2/neu antibodies versus calreticulin (CRT) that are bound to mBiNE after conjugation closely reflect the ratios of free proteins that were added to the reaction mixture before conjugation, suggesting the stoichiometric ratios of anti-HER2/neu antibodies and CRT as reactants are relatively predictive of the their final product contents for mBiNE. (B) Standard curves generated for concentration determination of both human and mouse anti-HER2/neu antibodies in solution. The standard curves are then used to determine the amount of unbound anti-HER2/neu proteins in solution after conjugation.

FIG. 16. Solution based characterization of free nanoparticles, nanoparticles conjugated with anti-HER2/neu antibodies alone, nanoparticles conjugated to calreticulin alone, and mBiNE.

Figure 17:
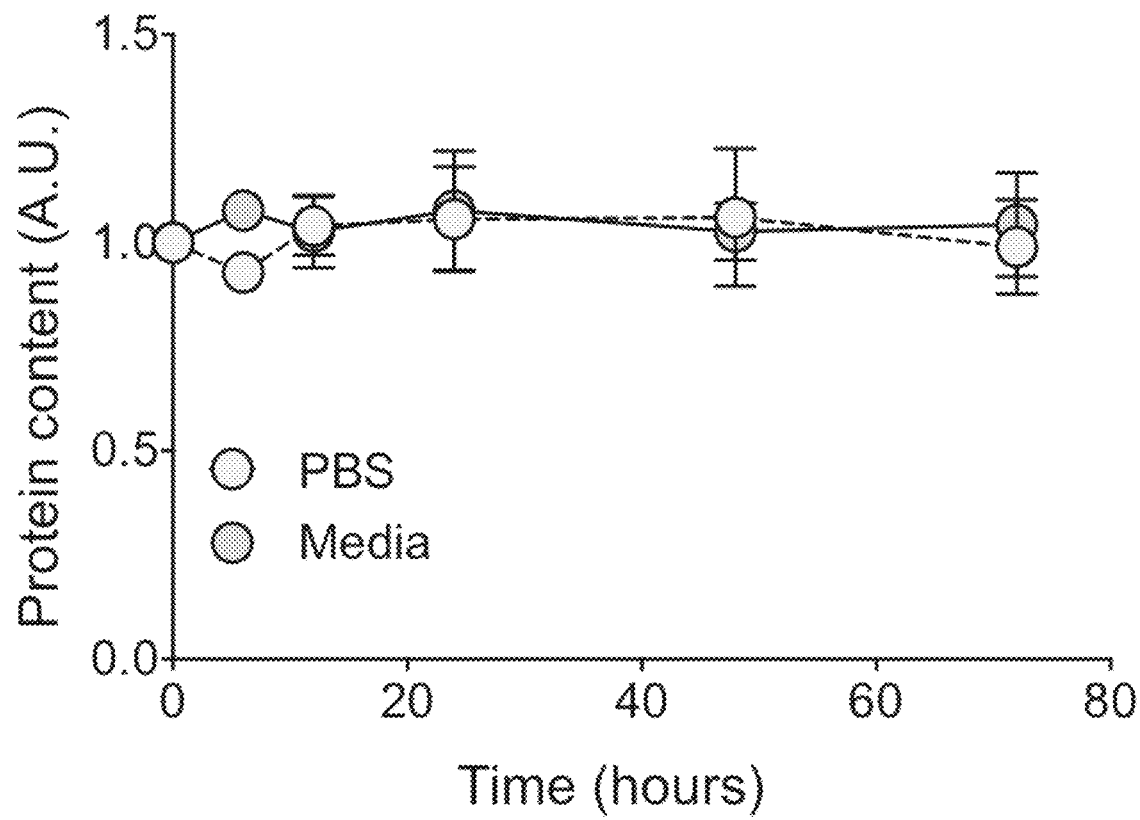

FIG. 17. Protein desorption assay of mBiNE in both PBS and cell culture media at 37° C. Error bars=standard deviation, n=3.

Figure 18:
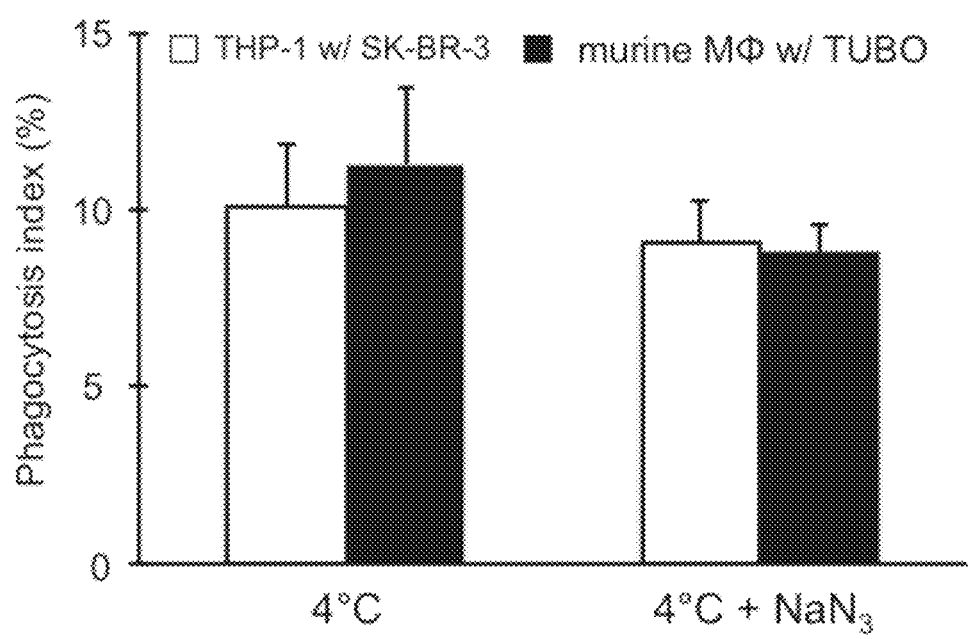

FIG. 18. Phagocytosis efficiencies of both human THP-1 and murine BALB/c macrophages against HER2/neu expressing SK-BR-3 or TUBO cells treated with mBiNE were significantly reduced when cultured at 4° C. or with the presence of 1% NaN3. Phagocytosis index is determined by comparing to macrophage uptake with respective tumor cells treated with mBiNE incubated at 37° C. without NaN3 treatment. Error bar=standard deviation, n=3.

Figure 19:
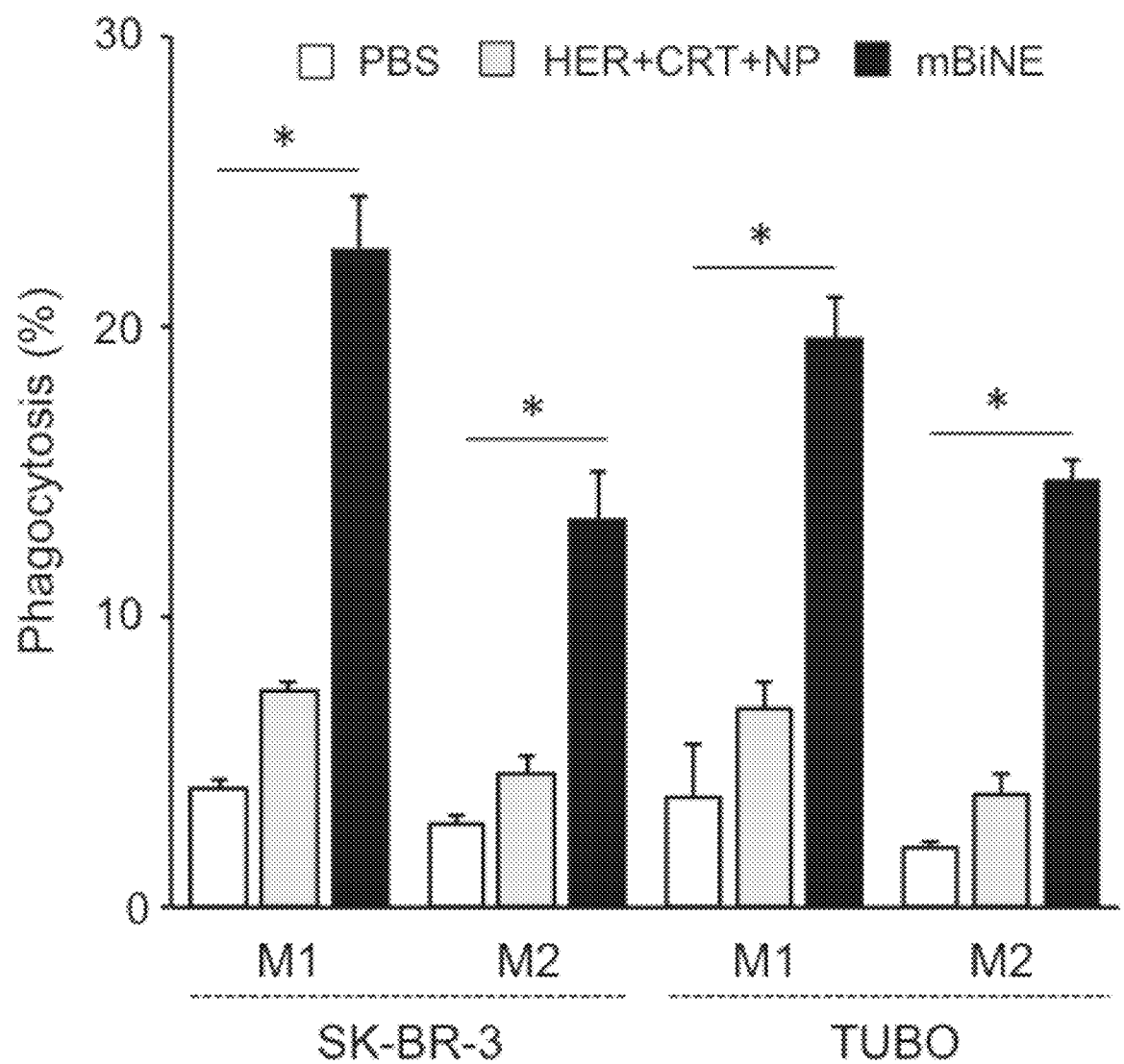

FIG. 19. Polarization status of macrophages did not alter mBiNE-induced phagocytosis activities. mBiNE-induced receptor-targeted phagocytosis against HER2/neu-expressing human (SK-BR-3) and mouse (TUBO) breast cancer cells by THP-1 or murine (BALB/c) bone marrow derived macrophages persisted for both M1 and M2 polarized phenotypes. Data presented as mean±standard deviation, n=5, $**P<0.01$ by one-way ANOVA.

Figure 20:
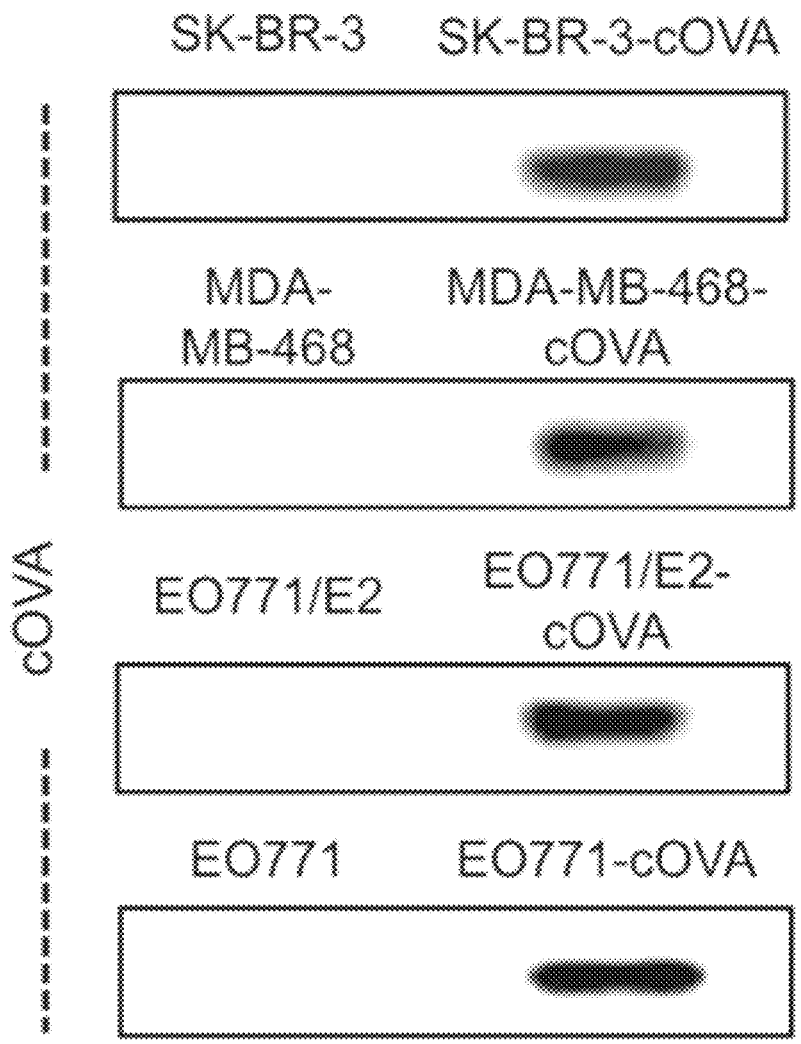

FIG. 20. Expression of cOVA in both human and mouse mammary carcinoma cell lines after lentiviral transduction.

Figure 21:
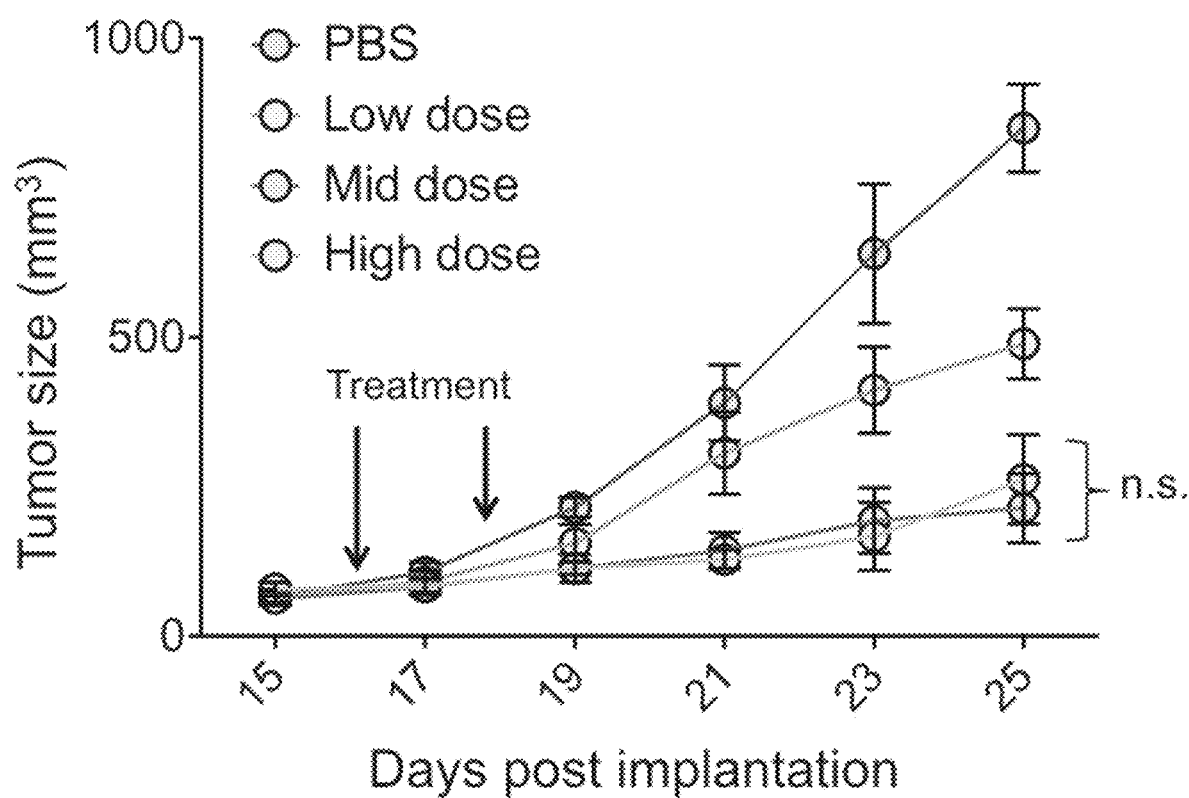

FIG. 21. Dosage determination for mBiNE in E0771/E2 tumor-bearing mice. All mBiNE doses were normalized to the total amount of anti-HER2 antibodies/CRT. All mBiNE had a HER:CRT ratio of 1:3. Low dose was about 0.5 mg/kg of anti-HER2 antibodies/CRT; mid dose was about 1.0 mg/kg of anti-HER2 antibodies/CRT; and high dose was about 2.0 mg/kg of anti-HER2 antibodies/CRT. No statistical significance in tumor growth was noted between mid-dose and high-dose treatment of mBiNE, therefore, the mBiNE dose with a corresponding anti-HER2 antibody/CRT concentration of 1.0 mg/kg was selected for all in vivo treatment experiments. Error bars=standard deviation, n=6.

Figure 22:
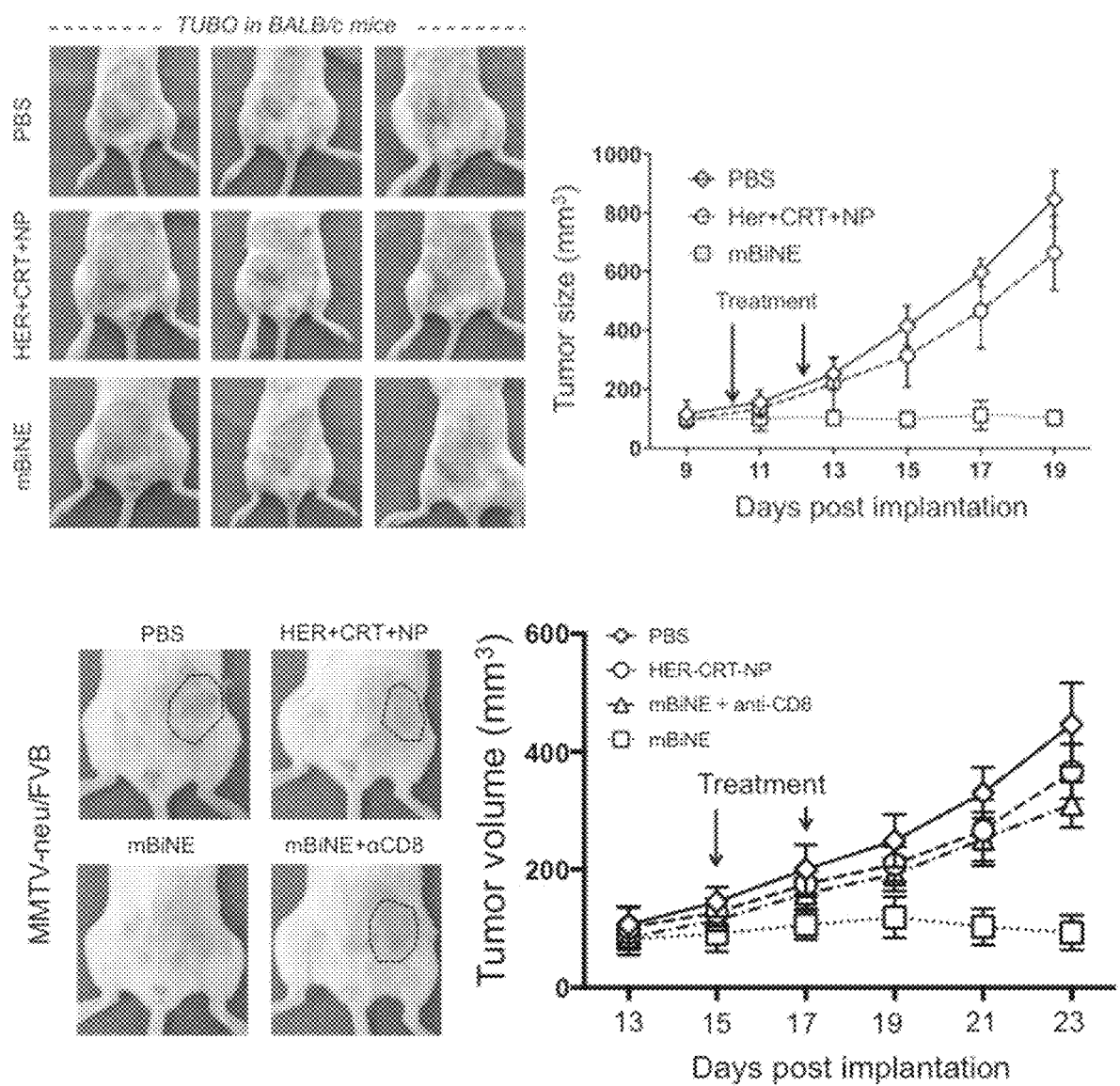

FIG. 22. mBiNE treatments inhibited tumor growth in TUBO tumour bearing BALB/c mice and MMTV-neu tumour bearing FVB mice, as compared to PBS or unconjugated anti-HER2/neu antibodies, CRT and nanoparticles. Error bars=standard deviation, n=5.

Figure 23:
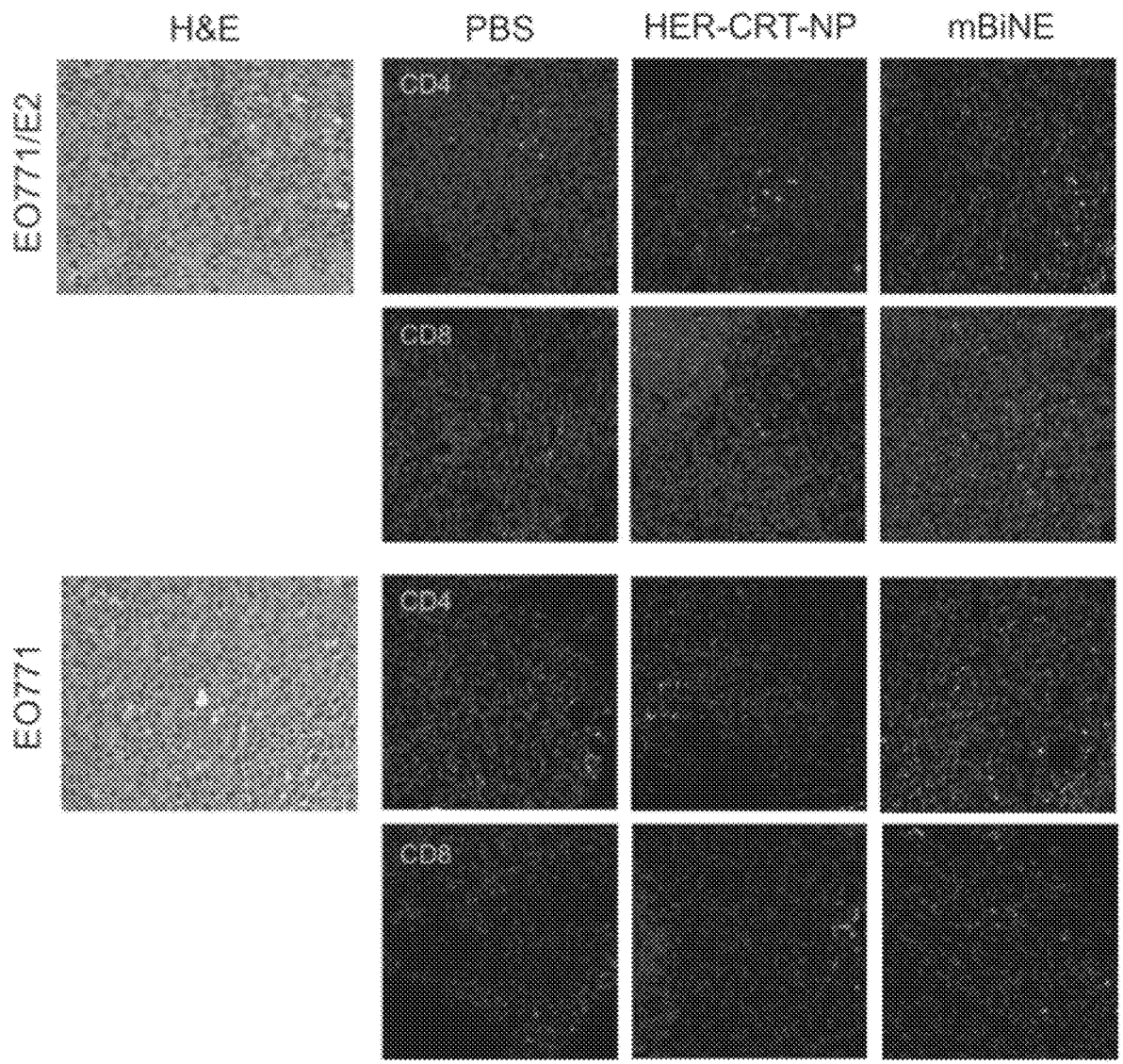

FIG. 23. Immunofluorescence staining for $CD4^+$ and $CD8^+$ T cells in HER2high E0771/E2 and HER2neg E0771 tumors after treatments with mBiNE or corresponding controls.

Figure 24:
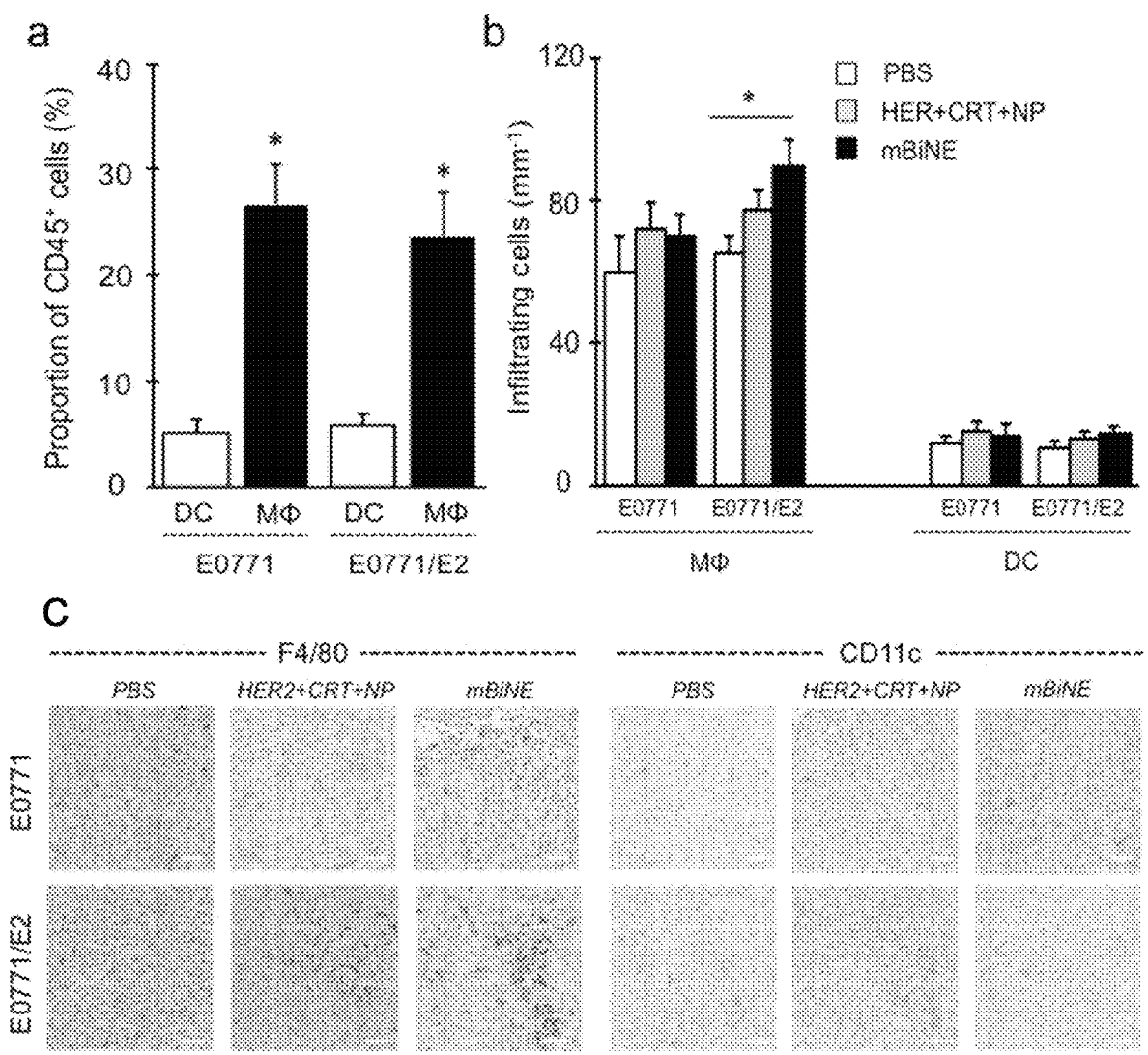

FIG. 24. Intratumoral macrophage (MΦ) and dendritic cell (DC) characterization upon mBiNE treatment. (a) Proportions of intratumoural MΦ and DC within $CD45^+$ enriched cells. The $CD11c^+CD11b^-$ DC population was analyzed given it has the greatest potential for cytotoxic T cell priming against cell-associated antigens via cross-presentation. (b) Both E0771 and E0771/E2 tumors have significantly higher degree of MΦ infiltration as compared to DCs. Data represented as mean±S.D., n=5, * denotes $p<0.05$, by unpaired Student's t-test. (c) Treatments with mBiNE significant increased the number of tumor infiltrating MΦ without changes in the number of DCs in E0771/E2 but not E0771 tumours. Scale bar=100 μm. Data represented as mean±S.D., n=5, * denotes $p<0.05$, by one-way ANOVA.

Figure 25:
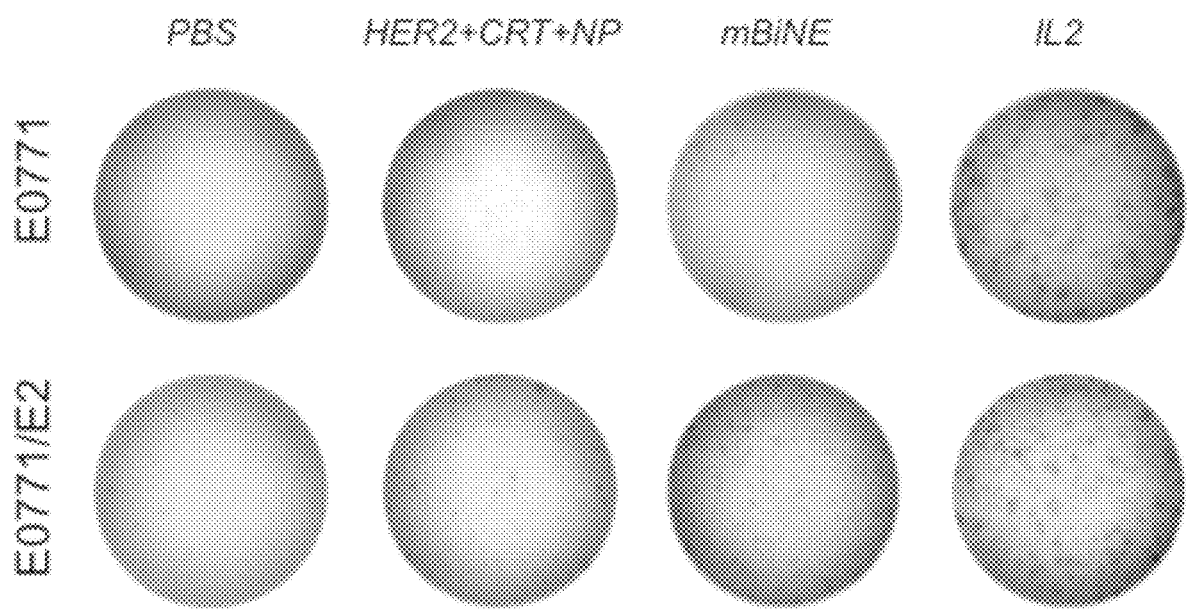

FIG. 25. Representative ELISPOT assay images showing the frequency of IFN-γ-producing $CD8^+$ T cells from E0771 and E0771/E2 tumours treated with PBS, unconjugated anti-HER2 antibody, free CRT and nanoparticles (HER2+CRT+NP), and mBiNE after co-culture with the same tumour cells, respectively. The $CD8^+$ T cells were stimulated using IL2 as a positive control.

Figure 26:
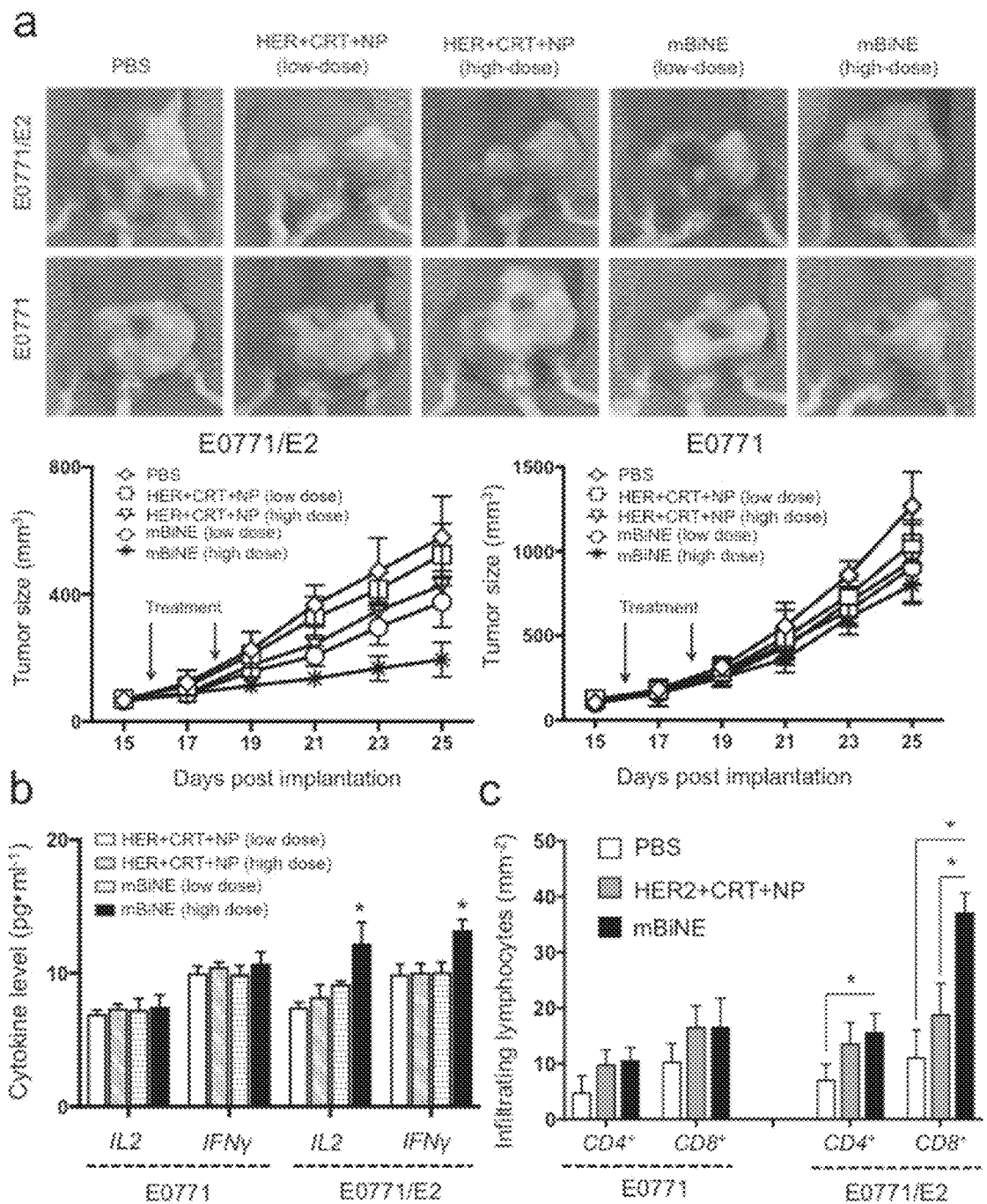

FIG. 26. Intravenously administered mBiNE induces anti-tumor effect and promote inflammatory cytokine responses. (a) Systemically delivered mBiNE induced anti-tumor effect in HER+E0771/E2 tumours, but required a higher dose (5 mg/kg) as compared to intratumoural delivery (1 mg/kg). (b) Peripheral blood cytokine analyses showed that systemic mBiNE treatment resulted in similar inflammatory cytokine activation as observed for intratumourally injected mBiNE. (c) Intratumoural immune cells showed systemic mBiNE treatment increased $CD8^+$ infiltration into E0771/E2 tumours. Data represented as mean±S.D., n=5, * denotes p<0.05, by one-way ANOVA or specified comparisons.

Figure 27:
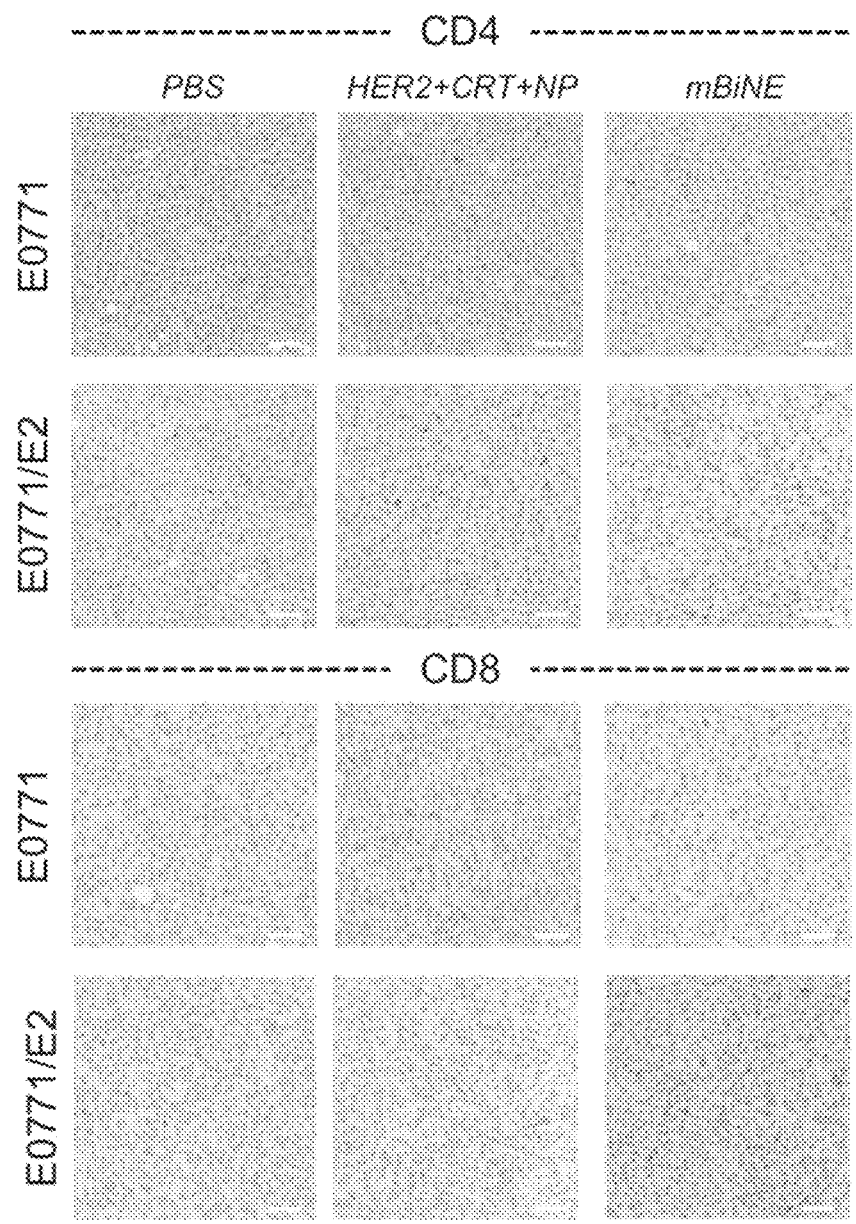

FIG. 27. IHC images of E0771 and E0771/E2 tumour stained for $CD4^+$ and $CD8^+$ T cells after treatments with intravenously administered PBS, unconjugated HER2+CRT+NP, and mBiNE. Scale bar=100 m.

Figure 28:
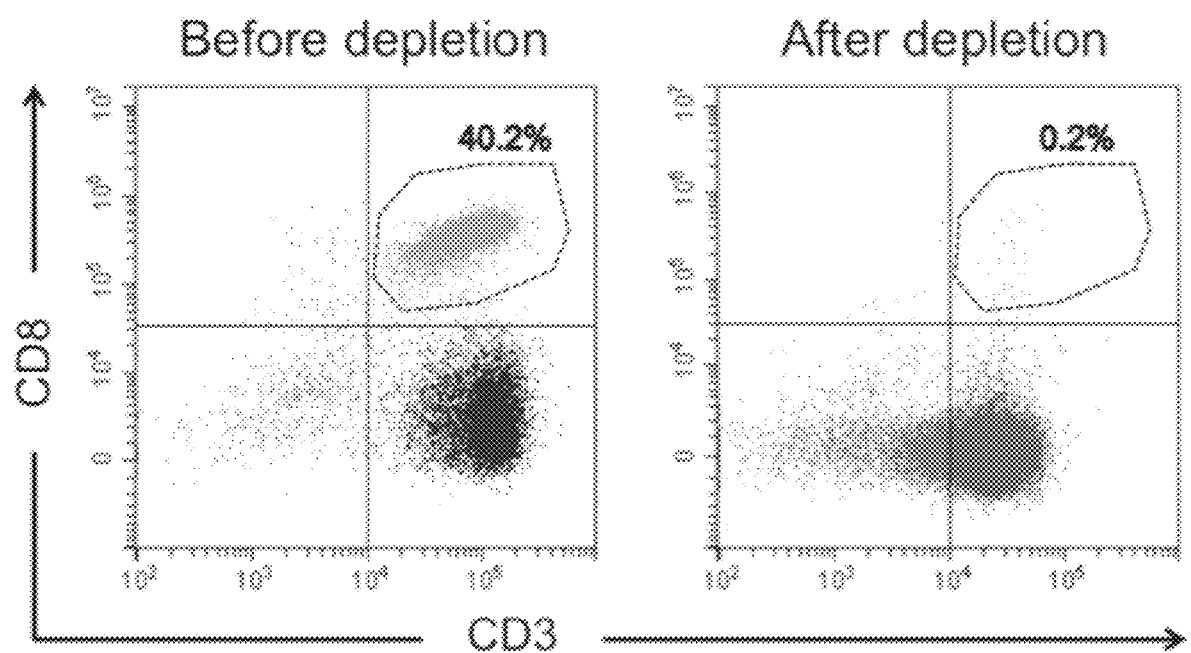

FIG. 28. Confirmation of successful $CD8^+$ T cell depletion using anti-CD8 antibodies in C57BL/6 mice.

Figure 29:
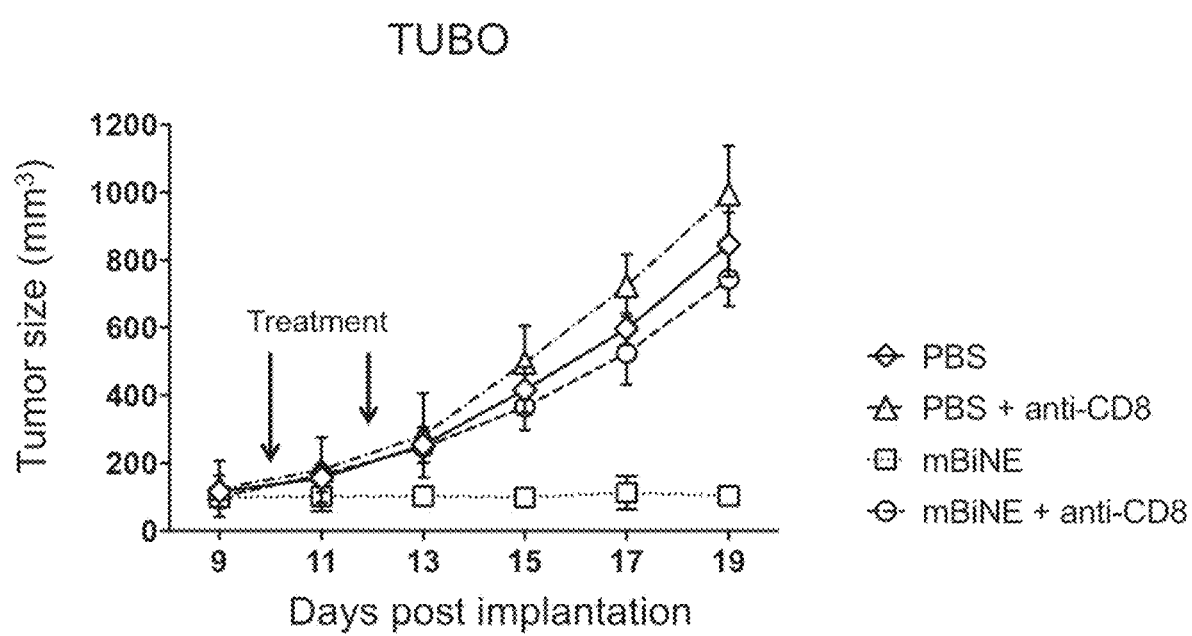

FIG. 29. Depletion of CD8 T cells abrogated the therapeutic effect of mBiNE in TUBO tumor bearing BALB/c mice. Error bars=standard deviation, n=5.

Figure 30:
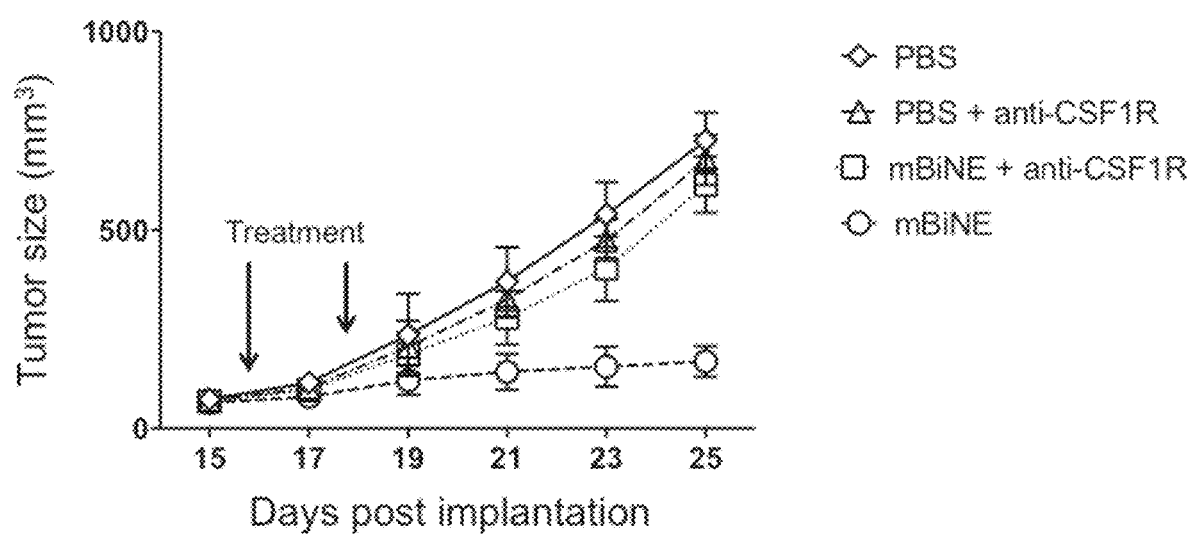

FIG. 30. Depletion of macrophages using anti-CSF1R antibodies drastically diminished the therapy effect of mBiNE in HER2-expressing E0771/E2 tumor bearing C57BL/6 mice. Error bars=standard deviation, n=5.

DETAILED DESCRIPTION

This document provides methods and materials involved in treating cancer. For example, this document provides methods and materials for using particles (e.g., nanoparticles) containing (a) one or more molecules having the ability to bind to a cancer cell (e.g., a human breast cancer cell) and (b) one or more molecules having the ability to bind to an APC (e.g., a human macrophage) to treat cancer.

The methods and materials provided herein can be used to treat any appropriate type of cancer. For example, the methods and materials provided herein can be used to treat breast cancer, brain cancer, prostate cancer, lung cancer, or colorectal cancer. In some cases, the methods and materials provided herein can be used to treat cancer (e.g., breast cancer) in any appropriate type of mammal including, without limitation, mice, rats, dogs, cats, horses, cows, pigs, monkeys, and humans.

In general, a particle (e.g., a nanoparticle) provided herein can be designed to include a molecule having the ability to bind to a cancer cell and a molecule having the ability to bind to an APC. Examples of molecules having the ability to bind to a cancer cell that can be used to make a particle provided herein (e.g., a nanoparticle) include, without limitation, DNA molecules, RNA molecules, antibodies such as anti-cancer antigen antibodies, non-antibody polypeptides, antibody fragments, vitamins, and recombinant proteins. Examples of DNA molecules having the ability to bind to a cancer cell that can be used to make a particle (e.g., a nanoparticle) provided herein include, without limitation, aptamers, oligonucleotides, and long strand nucleotide (>20 nucleotides). Examples of RNA molecules having the ability to bind to a cancer cell that can be used to make a particle (e.g., a nanoparticle) provided herein include, without limitation, aptamers, and long strand nucleotide (>20 nucleotides). Examples of anti-cancer antigen antibodies having the ability to bind to a cancer cell that can be used to make a particle (e.g., a nanoparticle) provided herein include, without limitation, anti-CD340 antibodies (e.g., anti-human epidermal growth factor receptor 2 (HER2) antibodies such as Herceptin), anti-EGFR antibodies (e.g., anti-human epidermal growth factor receptor antibodies), anti-EGFRviii antibodies (e.g., anti-human epidermal growth factor receptor variant 3 antibodies), anti-PSMA antibodies (e.g., anti-human prostate specific membrane antigen antibodies), anti-CEA antibodies (e.g., anti-human carcinoembryonic antigen antibodies), anti-CA125 antibodies (e.g., anti-human cancer antigen 125 antibodies), anti-CD20 antibodies (e.g., anti-human cluster antigen 20 antibodies), anti-CD30 antibodies, anti-CD33 antibodies, and anti-GD antibodies (anti-Gangliosides antibodies). In some cases, antibody fragments, nanobodies, full antibodies, or polypeptides can be used. Examples of non-antibody polypeptides having the ability to bind to a cancer cell that can be used to make a particle (e.g., a nanoparticle) provided herein include, without limitation, RGD polypeptides, EGFR-specific polypeptides, and HER2 polypeptides.

Examples of molecules having the ability to bind to an APC that can be used to make a particle provided herein (e.g., a nanoparticle) include, without limitation, DNA molecules, RNA molecules, antibodies, non-antibody polypeptides, and recombinant proteins. Examples of DNA molecules having the ability to bind to an APC that can be used to make a particle (e.g., a nanoparticle) provided herein include, without limitation, aptamers, oligonucleotides, and long strand nucleotide (>20 nucleotides). Examples of RNA molecules having the ability to bind to an APC that can be used to make a particle (e.g., a nanoparticle) provided herein include, without limitation, aptamers, oligonucleotides, and long strand nucleotide (>20 nucleotides). Examples of antibodies having the ability to bind to an APC that can be used to make a particle (e.g., a nanoparticle) provided herein include, without limitation, anti-LRP1 antibodies, anti-SIR-Palpha antibodies, and anti-complement receptor antibodies. In some cases, antibody fragments, nanobodies, or full antibodies can be used. Examples of non-antibody polypeptides having the ability to bind to an APC that can be used to make a particle (e.g., a nanoparticle) provided herein include, without limitation, CRT polypeptides, phosphatidylserine, and complement polypeptides. Examples of non-antibody polypeptides having the ability to bind to an APC that can be used to make a particle (e.g., a nanoparticle) provided herein include, without limitation, recombinant CRT, complement polypeptides, or bacterial polypeptides.

In some cases, a particle (e.g., a nanoparticle) provided herein can be designed as shown in FIG. 1. For example, a nanoparticle provided herein (e.g., a multivalent, bi-specific nanoparticle) can include an inner nanoparticle core conjugated to the targeting molecules. The particle (e.g., nanoparticle) or core can be of any appropriate geometrical shape. For example, a nanoparticle provided herein can be spherical, rod shaped, rectangular shaped, diamond shaped, or elliptical shaped. In some cases, a particle provided herein can range from about 1 nm to about 1000 nm in its longest dimension. The material composition of a particle (e.g., a nanoparticle) provided herein or a core of a particle (e.g., a nanoparticle) provided herein can include one or more metals, one or more metallic alloys, one or more semiconductor materials, one or more polymers, one or more lipids, one or more natural or synthetic proteins, or combinations thereof. For example, a particle (e.g., a nanoparticle) provided herein or a core of a particle (e.g., a nanoparticle) provided herein can be composed of polyethylene glycol, gold, silver, iron oxide, lipoproteins, polystyrene, poly(lactic-co-glycolic acid), poly(glycolic acid), poly(lactic acid), poly(e-caprolactone), polyamidoamine, polyhydroxybutyrate, chitosan, alginate, silica, or combinations thereof.

In some cases, a particle (e.g., a nanoparticle) provided herein or a core of a particle (e.g., a nanoparticle) provided herein can be doped or embedded with different types of therapeutic agents and/or contrast agent materials. For example, a particle (e.g., a nanoparticle) provided herein or a core of a particle (e.g., a nanoparticle) provided herein can be designed to include one, two, three, four, five, six, or more therapeutic agents. Examples of therapeutic agents that can be incorporated into a particle (e.g., a nanoparticle) provided herein include, without limitation, doxorubicin, cisplatin, carboplatin, temozolomide, docetaxel, and 5-FU. In some cases, a particle (e.g., a nanoparticle) provided herein or a core of a particle (e.g., a nanoparticle) provided herein can be designed to include one, two, three, four, five, six, or more contrast agent materials. Examples of contrast agent materials that can be incorporated into a particle (e.g., a nanoparticle) provided herein include, without limitation, gadolinium, iodide, iron oxide, FDG, radio-isotopes, and organic dyes.

In some cases, a particle (e.g., a nanoparticle) provided herein can include a surface coating. Such a surface coating can provide improved pharmacokinetic properties such as increased half-life of the particles within a mammal's body (e.g., a human's body). Examples of surface coatings that can be applied to a particle (e.g., a nanoparticle) provided herein include, without limitation, polyethylene glycol, recombinant CD47 polypeptides, and platelet derived cell surface polypeptides.

In some cases, the targeting molecules can be directly attached to one or more materials of the core of a particle (e.g., a nanoparticle) provided herein. In some cases, an intermediate bridge can be used to link the targeting molecules to one or more materials of the core of a particle (e.g., a nanoparticle) provided herein. Examples of materials or compounds that can be used as such intermediate bridges include, without limitation, complimentary nucleic acids, streptavidin-biotin, carboxylic acid-amines, antibody-antigen, and metal affinity ions such as thiolated polypeptides.

Any appropriate method can be used to attach targeting molecules to at least one material of the core of a particle (e.g., a nanoparticle) provided herein. For example, direct adsorption, ionic interactions, hydrophobic interactions, covalent bonding, or combinations thereof can be used.

In some cases, the ratio of APC targeting molecules to cancer cell targeting molecules can be about 1:1. In some cases, the ratio can be modified from 1:1 to 2:1, 3:1, 4:1, 5:1, and so on to provide more APC targeting molecules than cancer cell targeting molecules. In some cases, the ratio can be modified from 1:1 to 1:2, 1:3, 1:4, 1:5, and so on to provide less APC targeting molecules than cancer cell targeting molecules.

In some cases, a particle (e.g., a nanoparticle) provided herein can have the ability to facilitate the phagocytosis of cancer cells by APCs within a mammal's body and to activate down-stream adaptive immune responses (e.g., T cell responses) to treat cancer. For example, a particle (e.g., a nanoparticle) provided herein can be designed to recognize simultaneously cancer cells (which can deliver the nanoparticles to the area of interest, can limit non-specific immune reactions, and can spare normal surrounding tissues, thereby minimizing adverse effects) and APCs (which can enable these cells to initiate the first stages of a cancer cell clearance process). The ability to home and heighten the localization of APC's to the tumor microenvironment can increase tumor phagocytosis (e.g., tumor cell internalization). Once internalized, APCs can present fragments of the tumor antigens to the membrane surface via MHC molecules on the cell surface. This, in turn, can enhance T cell recognition of the cancer cells within a mammal. See, e.g., FIG. 2.

As described herein, a particle (e.g., a nanoparticle) provided herein can be administered a mammal to treat cancer. Any appropriate method can be used to administer a particle (e.g., a nanoparticle) provided herein to a mammal. For example, a particle (e.g., a nanoparticle) provided herein can be administered via injection (e.g., subcutaneous injection, intramuscular injection, intravenous injection, or intrathecal injection).

Before administering a particle (e.g., a nanoparticle) provided herein to a mammal, the mammal can be assessed to determine whether or not the mammal has cancer (e.g., breast cancer). Any appropriate method can be used to determine whether or not a mammal has cancer. For example, a mammal (e.g., human) can be identified as having cancer using standard diagnostic techniques. In some cases, a tissue biopsy can be collected and analyzed to determine whether or not a mammal has cancer.

After identifying a mammal as having cancer (e.g., breast cancer), the mammal can be administered a composition containing particles (e.g., nanoparticles) provided herein. For example, a composition containing particles (e.g., nanoparticles) provided herein can be administered prior to or in lieu of surgical resection of a tumor. In some cases, a composition containing particles (e.g., nanoparticles) provided herein can be administered following resection of a tumor.

A composition containing particles (e.g., nanoparticles) provided herein can be administered to a mammal in any appropriate amount, at any appropriate frequency, and for any appropriate duration effective to achieve a desired outcome (e.g., to increase progression-free survival). In some cases, a composition containing particles (e.g., nanoparticles) provided herein can be administered to a mammal having cancer (e.g., breast cancer) to reduce the progression rate of the cancer by 5, 10, 25, 50, 75, 100, or more percent. For example, the progression rate can be reduced such that no additional cancer progression is detected. Any appropriate method can be used to determine whether or not the progression rate of cancer is reduced. For example, the progression rate of cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate was reduced.

In some cases, a composition containing particles (e.g., nanoparticles) provided herein can be administered to a mammal having cancer (e.g., breast cancer) under conditions where progression-free survival is increased (e.g., by 5, 10, 25, 50, 75, 100, or more percent) as compared to the median progression-free survival of corresponding mammals having untreated cancer (e.g., untreated breast cancer). Progression-free survival can be measured over any appropriate length of time (e.g., one month, two months, three months, four months, five months, six months, or longer).

An effective amount of a composition containing particles (e.g., nanoparticles) provided herein can be any amount that reduces the progression rate of cancer (e.g., breast cancer), increases the progression-free survival rate, or increases the median time to progression without producing significant toxicity to the mammal. Typically, an effective amount of a composition containing particles (e.g., nanoparticles) provided herein can be from about 100 mg/m$^2$ to about 200 mg/m$^2$. If a particular mammal fails to respond to a particular amount, then the amount of a composition containing particles (e.g., nanoparticles) provided herein can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer (e.g., breast cancer) may require an increase or decrease in the actual effective amount administered.

The frequency of administration can be any frequency that reduces the progression rate of cancer (e.g., skin cancer), increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition containing particles (e.g., nanoparticles) provided herein can include rest periods. For example, a composition containing particles (e.g., nanoparticles) provided herein can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition containing particles (e.g., nanoparticles) provided herein can be any duration that reduces the progression rate of cancer (e.g., breast cancer), increases the progression-free survival rate, or increases the median time to progression without producing significant toxicity to the mammal. Thus, the effective duration can vary from several days to several weeks, months, or years. In general, the effective duration for the treatment of cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer (e.g., breast cancer).

A composition containing particles (e.g., nanoparticles) provided herein can be in any appropriate form. For example, a composition containing particles (e.g., nanoparticles) provided herein can be in the form of a solution or powder with or without a diluent to make an injectable suspension. A composition containing particles (e.g., nanoparticles) provided herein also can contain additional ingredients including, without limitation, pharmaceutically acceptable vehicles. A pharmaceutically acceptable vehicle can be, for example, saline, water, lactic acid, mannitol, or combinations thereof.

After administering a composition containing particles (e.g., nanoparticles) provided herein to a mammal, the mammal can be monitored to determine whether or not the cancer (e.g., breast cancer) was treated. For example, a mammal can be assessed after treatment to determine whether or not the progression rate of cancer was reduced (e.g., stopped). As described herein, any method can be used to assess progression and survival rates.

The invention will be further described in the following examples, which do not limit the scope of the invention described in the claims.

EXAMPLES

Example 1—Multivalent Bi-Specific Nanoparticles Enable Specific Phagocytic Clearance of Cancer Cells and Promote Durable Anti-Tumor Immunity Cell Culture Macrophages were extracted from the bone marrow of C57/BL6 mice femurs and maintained in the medium containing 48% DMEM (Corning), 30% L929 (Stony Brook Cell Culture/Hybridoma facility), 20% fetal bovine serum (FBS) (Sigma), 1% sodium pyruvate (Gibco), and 1% penicillin/streptomycin (P/S) (Gibco). T cells were extracted from the spleen of OT-1 transgenic mice and purified using the T cell isolation kit (Stem Cell Technologies). E0771/E2 cells were obtained from Prof. Jun (University of Louisville). 4T-1 cells were obtained from Prof. Knudsen (Mayo Clinic, Florida). SKBR-3 (ATCC) cells were maintained in McCoy's 5a medium modified with 1.5 mM L-glutamine (Invitrogen), supplemented with 10% FBS and 1% P/S. Primary T cells, TUBO cells (ATCC), MDA-MB-468 cells (ATCC), and 4T-1 cells were cultured in RPMI 1640 (Fisher), 10% FBS, and 1% P/S. Cell cultures were incubated at 37° C. and equilibrated in 4% $CO_2$ and air.

Animals

C57/BL6, Balb/C, and OT-1 TCR mice were purchased from Jackson Laboratory and maintained at an animal facility in a specific-pathogen-free environment. Typically, 6 to 8 week old mice were used.

Nanoparticle Conjugation

Carboxylated polystyrene nanoparticles (NP) having a diameter of about 30 nm and labeled with fluorescence were purchased from Magsphere (Pasadena, Calif.). Conjugation of NP with anti-CD340 (i.e., anti-receptor tyrosine-protein kinase erbB-2) antibodies (e.g., Trastuzumab (tradename Herceptin); both anti-human HER2 antibodies and anti-mouse Erbb2 antibodies were individually used) and/or CRT polypeptides (both human CRT polypeptides and mouse CRT polypeptides were obtained from Abcam and used individually) was performed using carbodiimide-mediated chemistry (Jiang et al., *Chemistry of Materials*, 18(4):872-878 (2006)). Briefly, NP were diluted in PBS to a final concentration of 100 nM (based on the stock solution of 2.5% solid). A 1:10 ratio of nanoparticle:antibodies/polypeptides (anti-CD340 antibodies alone, CRT polypeptides alone, or a mixture of both anti-CD340 antibodies and CRT polypeptides) molar mixture was reacted with a 100:1 molar ratio of N-(3-Dimethylaminopropyl)-N'-ethylcarbodiimide (EDC) (Sigma-Aldrich)/N-Hydroxysulfosuccinimide (sulfo-NHS) (Sigma-Aldrich): nanoparticle for 2 hours. The solution was then washed three times with 50 KD or 100 KD molecular weight cut-off centrifugal filter (Millipore) at 4500 RPM for 5 minutes to remove excess unreacted molecules. The resulting pellet was centrifuged down at 6000 RPM for 10 minutes and re-suspended in PBS. Concentrations of anti-CD340 antibodies and/or CRT polypeptides after conjugation were measured using NanoDrop (Thermo Scientific). For all treatment conditions, the concentration of proteins (free and modified) was kept constant at 20 µg/mL. Solution-based characterizations of NP size and charge distributions were measured using Zeta-Sizer Nano instrument (Malvern). Gel electrophoresis of NP after conjugation was performed with 0.5-1% agarose gel, running at 100V for 30 minutes and imaged with gel imager (Typhoon, GE healthcare).

Phagocytosis Assay

Phagocytosis assays were performed by incubating macrophage and tumor cells with or without NP conjugated with anti-CD340 antibodies alone, CRT polypeptides alone, or a mixture of both anti-CD340 antibodies and CRT polypeptides. The tumor cells were harvested and re-suspend in $1\times10^6$ cells/mL in PBS/0.1% BSA and incubated with 1 mM cell trace CFSE (Life Technology) at 37° C. for 10 minutes in the dark. The staining was quenched by adding 5 volumes of ice-cold culture media to the cell and incubating them on ice for 5 minutes. After a total wash of three times with fresh medium, the $5\times10^5$ cells were plated in a 12-well cell culture plate (Corning). After 2 hours, $1.5\times10^6$ macrophages stained with eFluor® 670 (eBioscience) were added and incubated for 4 hours at 37° C. together with free antibodies (e.g., anti-CD340 antibodies alone or CRT polypeptides alone) or nanoparticles containing antibodies and/or polypeptides (NP conjugated with anti-CD340 antibodies alone, NP conjugated with CRT polypeptides alone, or NP conjugated with both anti-CD340 antibodies and CRT polypeptides).

The percentage of phagocytosis was analyzed using Accuri C6 (BD Bioscience), and calculated as the percentage of CFSE$^+$ cells within eFluor 670$^+$ macrophages. For imaging observation, $1\times10^5$ tumor cells with CFSE were firstly plated in coverslip bottom culture chamber (LabTEK). After 2 hours, $3\times10^5$ macrophages and free antibodies, free polypeptides, or NPs were added and incubated for 4 hours at 37° C. The cells then were fixed with 4% w/v formaldehyde for 30 minutes at room temperature. After that, the cells were washed with PBS for three times and incubated with the surface marker of macrophage (CD11b; APC tag, Bio Legend) for 30 minutes at 37° C. The images were observed using the Zeiss LSM 710 laser-scanning microscope with a 40× oil emersion objective, NA 1.2 (Carl Zeiss).

Antigen Presentation and T Cell Activation

Tumor cells transfected with pLenti-cOvalbumin (provided by CAV) were co-cultured with macrophages for 3 days in the presence of NPs conjugated with both anti-CD340 antibodies and CRT polypeptides. Then, SIINFEK6/H-2Kb (APC tag, eBioscience), which specifically reacts with ovalbumin-derived peptide SIINFEKL bound to H-2Kb of MHC class I, but not with unbound H-2Kb or H-2Kb bound with an irrelevant peptide, was used to detect and quantify antigen presentation. For T cell activation, the cells were obtained from Balb/C mice. E0771/E2 cells were co-cultured with macrophage for 3 days, and then fresh extracted naïve T cells were added and incubated for another 2 days. T cells were identified with anti-CD3 antibodies and anti-CD8 antibodies, and the activation was distinguished using anti-CD44 antibodies and anti-CD62L antibodies.

Results

Design of the Multivalent, Bi-Specific Nanoparticles

Figure 3:
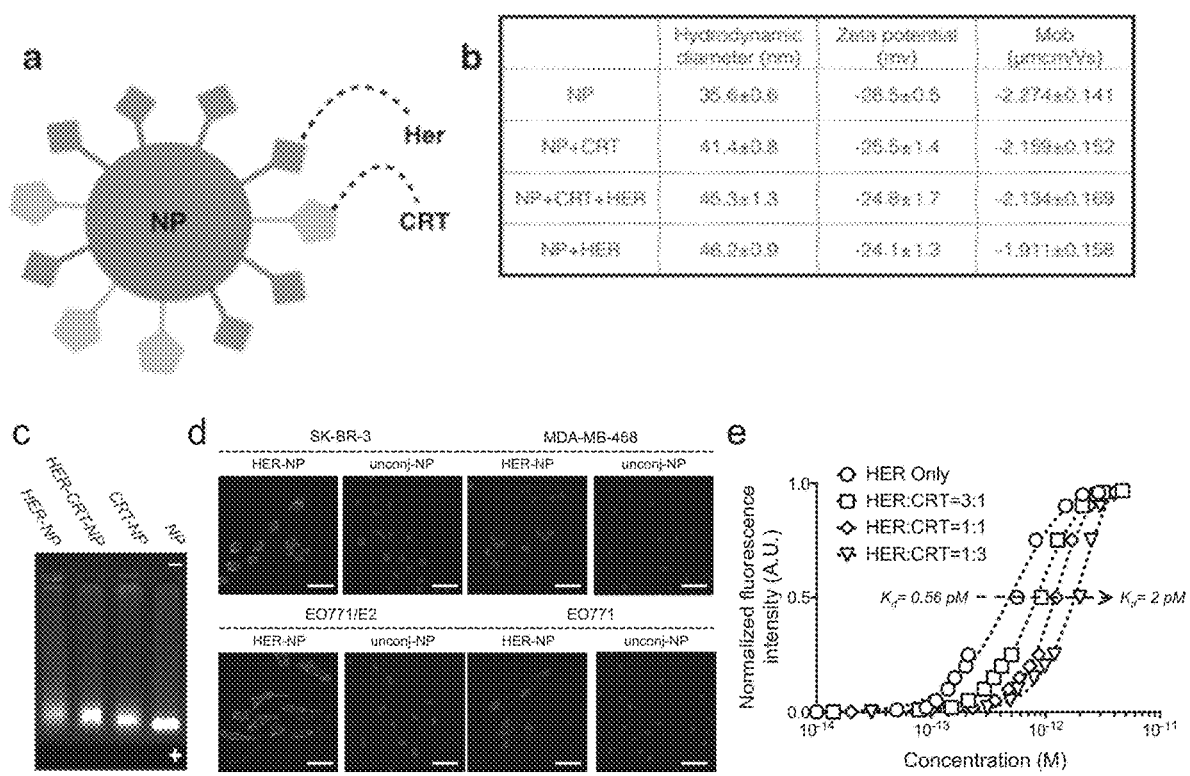
FIG. 3. Nanoparticle conjugate characterization and tumor cell-specific targeting of a multivalent nanoparticle (NP) presenting anti-Her2 antibody (Her) and calreticulin (CRT). Physical characteristics of nanoparticles (a) were measured using a solution-based testing of hydrodynamic diameter (b), nanoparticle charge (b), and gel electrophoresis (c) assays. SKBR3 human breast cancer cell lines that are known to overexpress HER2 were incubated with nanoparticles coated with Herceptin (NP+Her) to demonstrate specific cell membrane interactions between NP+Her and HER2$^+$ cells (d), compared to cells that lack HER2 expression (MDA-MB-468) (d). Nuclear staining was revealed using a blue staining, while nanoparticles (NP+Her) were observed using a red stain. (e) When adjusting the ratio of anti-Her2 antibodies and CRT conjugated to the nanoparticle, the binding avidity of the nano-conjugates changed. When only Her2 antibody were conjugated to the nanoparticle, the resulting product had the strongest binding capacity towards the HER2$^+$ tumor cells. This binding strength decreased as the content of CRT was increased as demonstrated by an increase in the dissociation constant $K_d$.

Multivalent, bi-specific nanoparticles were constructed by conjugating antibodies (e.g., anti-CD340 antibodies) and polypeptides (e.g., CRT polypeptides) to polymer nanoparticles (FIG. 3a). For example, nanoparticles were surface modified with anti-CD340 antibodies (e.g., anti-human HER2 antibodies; hereafter referred to as NP-HER) to enable specific targeting of to HER2 receptors that are overexpressed in certain breast cancers. This tumor-specific targeting can enable delivery and targeting of the nanoparticle to the cancer site. The nanoparticles were further surface modified with recombinant CRT polypeptides. CRT polypeptides are over-expressed by stressed cells under normal physiological conditions to promote phagocytic clearance by macrophages. Cancer cells also up-regulate CRT polypeptide expression on their surface, but is able to prevent phagocytosis by macrophages through expression of CD47 polypeptides. The balance of the CRT-CD47 axis can determine cancer cell phagocytic eradication or cancer cell evasion of phagocytosis.

Carboxylic acid terminated, fluorescently labeled, polystyrene nanoparticles were used to create nanoparticles successfully conjugated to anti-CD340 antibodies and CRT polypeptides (FIG. 3a-e; HER represents anti-CD340 antibody). The final conjugated product was monodisperse in solution as demonstrated by the narrow band from Agarose gel electrophoresis and maintained its fluorescence properties (FIG. 3a-e). The conjugated nanoparticles also exhibited targeting specificity towards HER2 positive cancer cells (FIG. 3e). See, also, FIGS. 14a-c.

The conjugation efficiency of anti-HER2 antibody and CRT onto the nanoparticle closely reflected the stoichiometric ratios of the proteins in solution despite the difference in their molecular weights (FIGS. 15a-b).

Depending on the final ratio of anti-HER2 antibody and CRT contents, the mBiNE had a hydrodynamic diameter of approximately 45 nm with a slightly anionic surface charge (between −24 and −28 mv) (FIG. 16). The mBiNE was highly stable in aqueous environments with minimal protein desorption even after prolonged incubation in aqueous solutions (FIG. 17).

Figure 4:
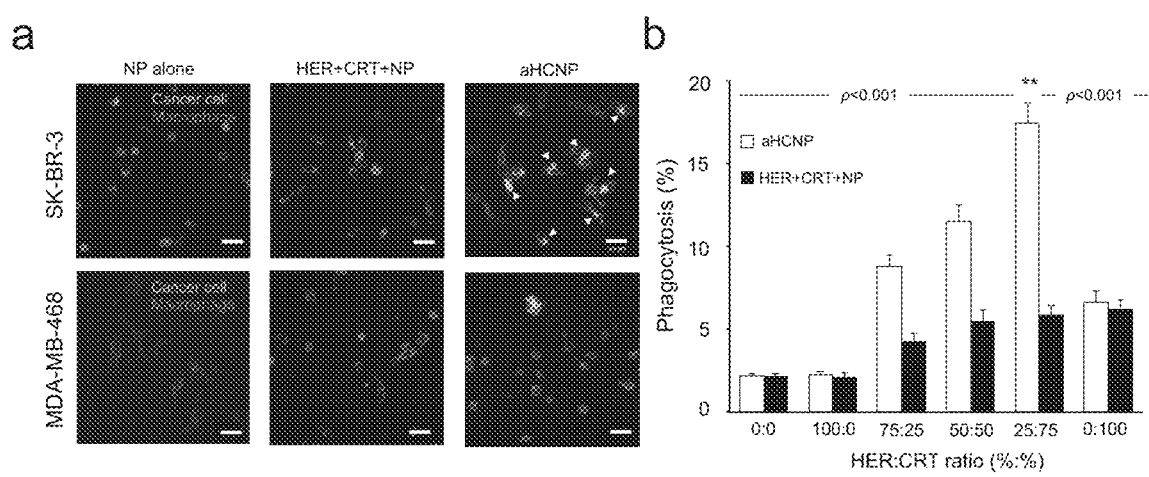
FIG. 4. Modulation of macrophage phagocytosis activity using nanoparticles. (a) Breast cancer cells overexpressing HER2 receptors (SKBR3, green), were incubated with macrophages (red). (b) Low rates of tumor cell internalization were observed with unconjugated nanoparticles (NP alone) or with incubation with a mixed solution of Herceptin, calreticulin and nanoparticles (HER+CRT+NP). The rate of phagocytosis was controlled using different ratios of anti-CD340 antibodies to CRT polypeptides. By varying the ratio of anti-CD340 antibodies to CRT on the surface, the degree of tumor cell internalization/phagocytosis by the macrophages was controlled. Nanoparticles aHCNP conjugated with three times more CRT than anti-CD340 antibodies (3:1 ratio of CRT to antibodies) exhibited the greatest induction of phagocytosis (about 6-fold increase) compared to baseline.

Different ratios of CRT polypeptides to anti-CD340 antibodies were tested to determine an optimum combination for specific phagocytosis of HER2 over-expressing breast cancer cells (FIG. 4). A CRT:anti-CD340 antibody ratio of 3:1 resulted in enhanced phagocytic clearance of HER2 over-expressing SKBR3 breast cancer cells (FIG. 4).

Figure 5:
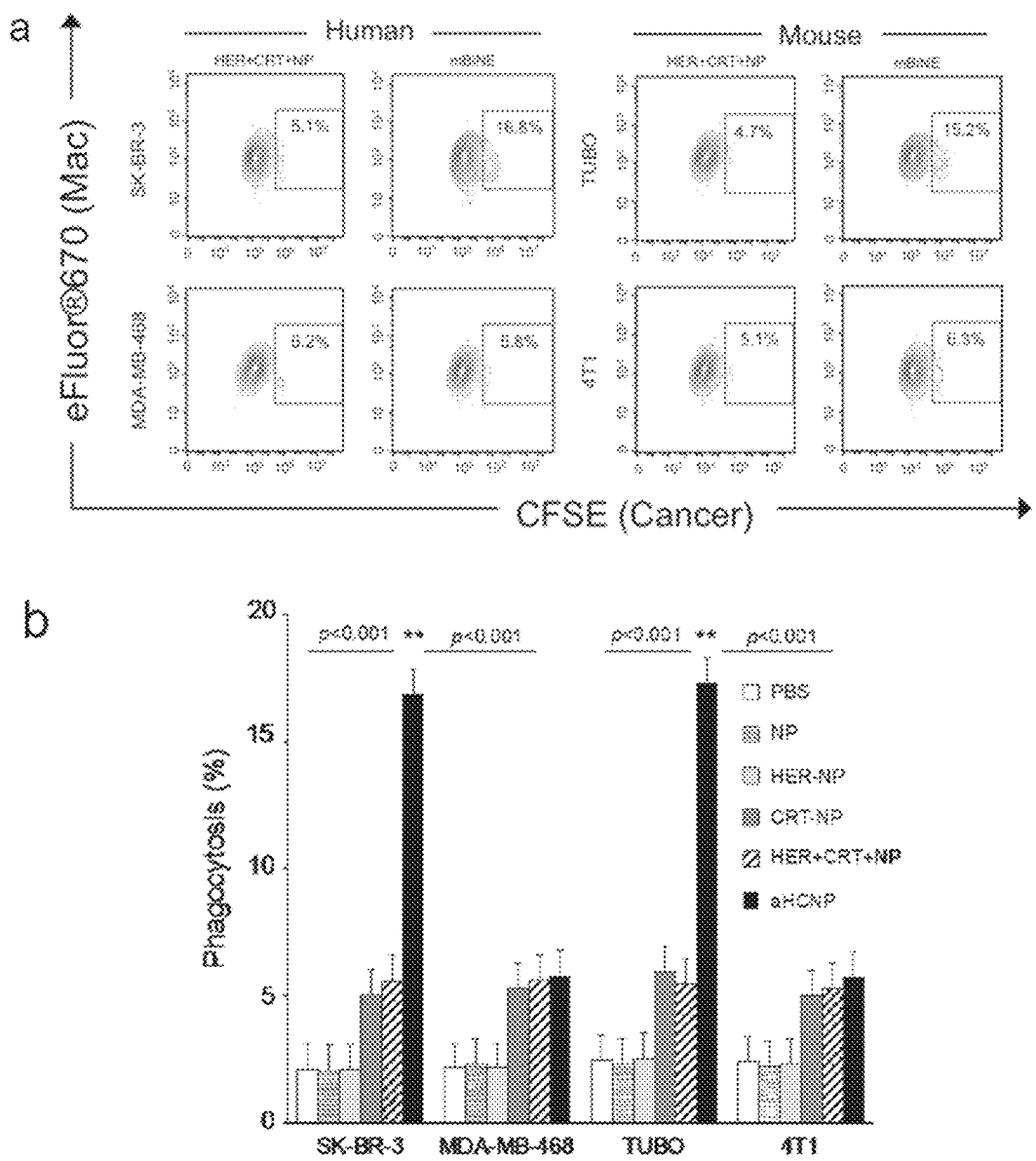
FIG. 5. Nanoparticles promote enhanced phagocytosis and tumor clearance in both human and mouse breast cancer cells including the HER2 overexpressing SKBR-3, TUBO and HER2 negative MDA-MB-468 and 4T1 cell lines (a, b).
Figure 6:
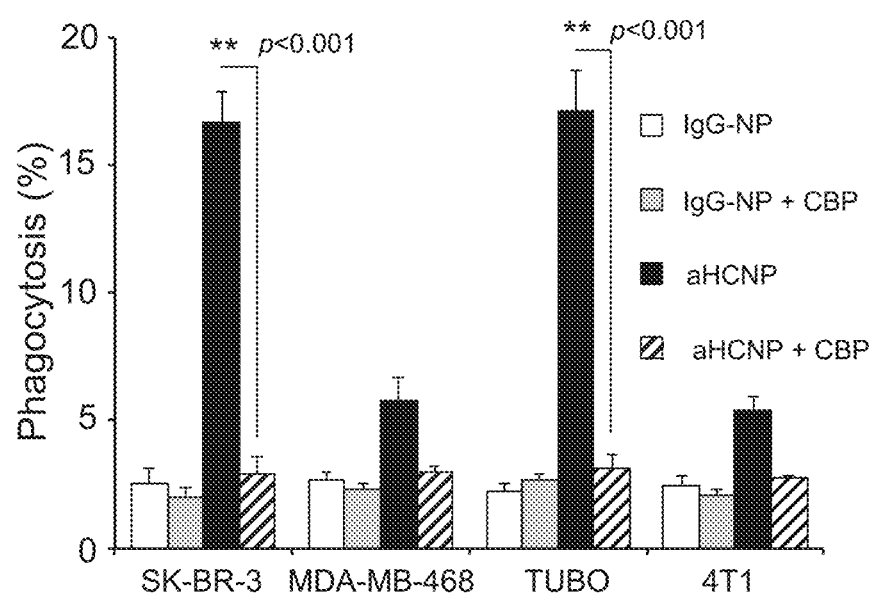
FIG. 6. Treatment of the breast cancer cells with calreticulin blocking peptide (CBP) abrogated the enhanced phagocytosis effect mediated by aHCNP (also referred to herein as a multivalent bi-specific nano-bioconjugate engager (mBiNE)), suggesting CRT is critical in mediating the phagocytic response.

Multivalent Bi-Specific Nanoparticles Promote Selective Phagocytosis of Cancer Cells by Macrophages The following was performed to test whether nanoparticles conjugated with anti-CD340 antibodies and CRT polypeptides promote specific phagocytosis of HER2 over-expressing breast cancer cells as compared to HER2 non-expressing breast cancer cells or as compared to normal cells. The nanoparticles conjugated with anti-CD340 antibodies and CRT polypeptides (aHCNP; also referred to herein as a multivalent bi-specific nano-bioconjugate engager (mBiNE)) exhibited significantly increased phagocytosis of HER2 over-expressing SKBR3 cancer cells as compared to NP alone, CRT-NP, HER-NP, and uncongugated NP in the presence of free CRT and HER (HER+ CTR+NP) (FIG. 5). The nanoparticles conjugated with anti-CD340 antibodies and CRT polypeptides (aHCNP) also exhibited significantly increased phagocytosis of HER2 over-expressing SKBR3 cancer cells as compared to HER2 low-expressing MDA-MB-468 cells (FIG. 5). Soluble CRT alone can activate macrophages through the interaction with lipoprotein like receptor 1 (LRP-1) to promote phagocytosis of cancer cells. The results provided herein, however, demonstrate that the linkage of CRT polypeptides and agents having the ability to bind to cancer cells (e.g., anti-CD340 antibodies) to nanoparticles results in nanoparticles with enhanced phagocytosis activities against cancer cells in a specific manner. The enhanced phagocytosis activity mediated by nanoparticles conjugated with anti-CD340 antibodies and CRT polypeptides (aHCNP) was mediated via CRT signaling with the macrophages since the blockade of the CRT-LRP1 interaction with CRT blocking agent removed this effect in both mouse and human HER2 over-expressing cell lines (FIG. 6).

Repeating the experiments at 4° C. or with NaN3 drastically reduced the phagocytotic efficiency of both THP-1 and murine macrophages against SK-BR-3 and TUBO cells (FIG. 18). Given that macrophage functions were strongly affected by its polarization status, it was determined whether mBiNE-induced cancer cell phagocytosis depends on specific macrophage phenotype. The enhanced cancer cell phagocytotic activities by mBiNE treatment were also observed for both activated M1 and M2 macrophages, which were stimulated with lipopolysaccharide (LPS) and IL4, respectively (FIG. 19).

Figure 7:
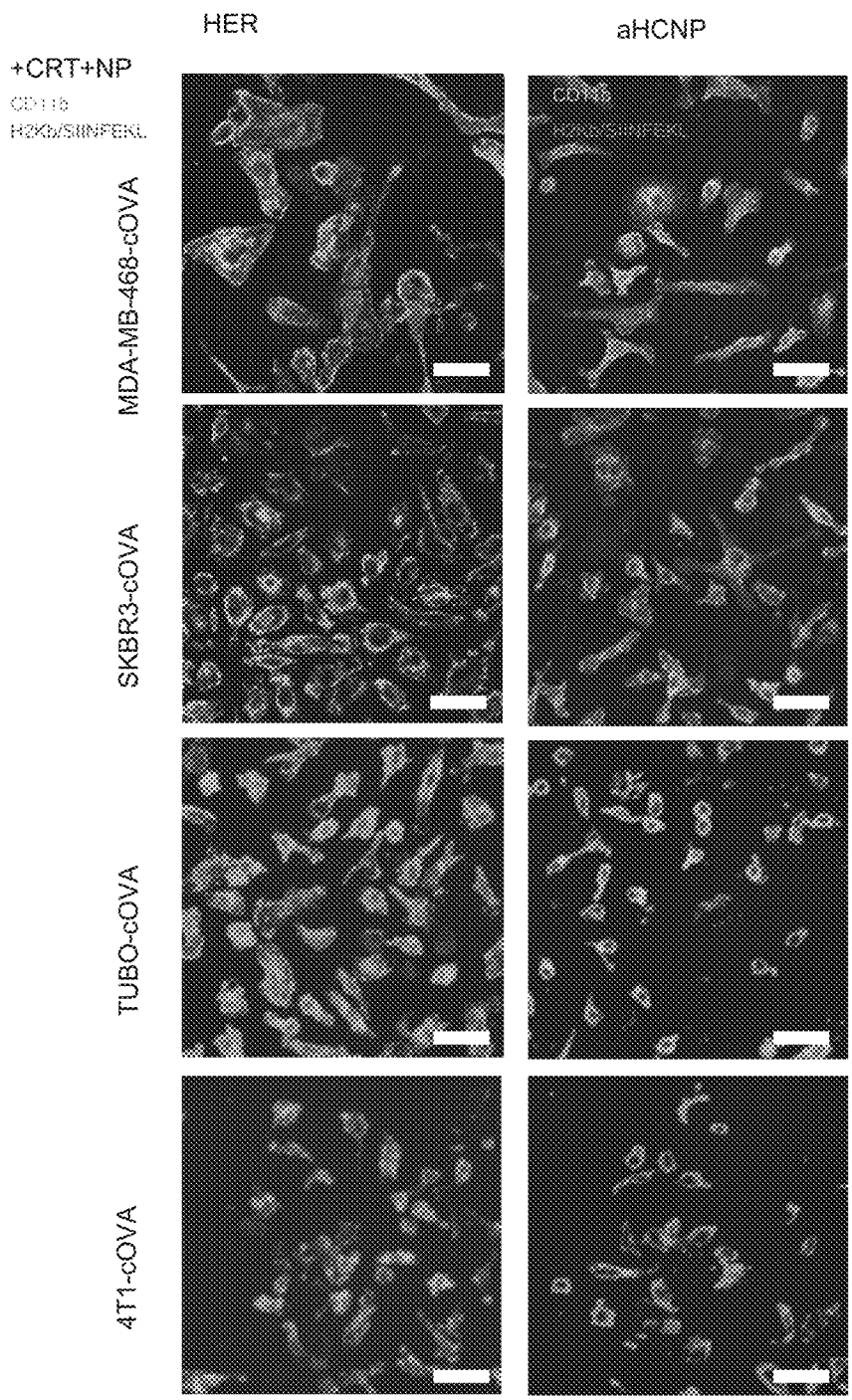
FIG. 7. Tumor-specific antigen presentation is enhanced following treatment with nanoparticles. Three different cell lines (human SKBR3, mouse TUBO, and mouse N202 cell lines), which over express CD340 were stably transfected to express chicken ovalbumin (c-ova) and tested for antigen presentation. Any tumor cells phagocytosed would therefore present c-ova peptide fragments on membrane-bound MHC class I of the APCs. An antibody was used to detect ova-derived peptide (SIINFEKL)-bound to H-2Kb of MHC class 1. This antibody does not detect unbound H-2Kb or H-2Kb bound with an irrelevant peptide. Tumor cells were incubated with or without NP+HER+CRT and then incubated with macrophages. Cells treated with NP+HER+CRT exhibited a significant increase in macrophage staining with the MHC-Ova antibody (anti-SIINFEKL peptide bound to H-2Kb antibody labeled with PE). Increased antigen presentation was observed in all three cell lines treated with NP+HER+CRT (left peaks) as compared to those not treated with NP+HER+CRT (right peaks) on flow cytometry analysis. Immunohistochemistry demonstrated increased ova peptide presentation in cells treated with NP+HER+CRT as compared to those not treated with NP+HER+CRT.
Figure 8:
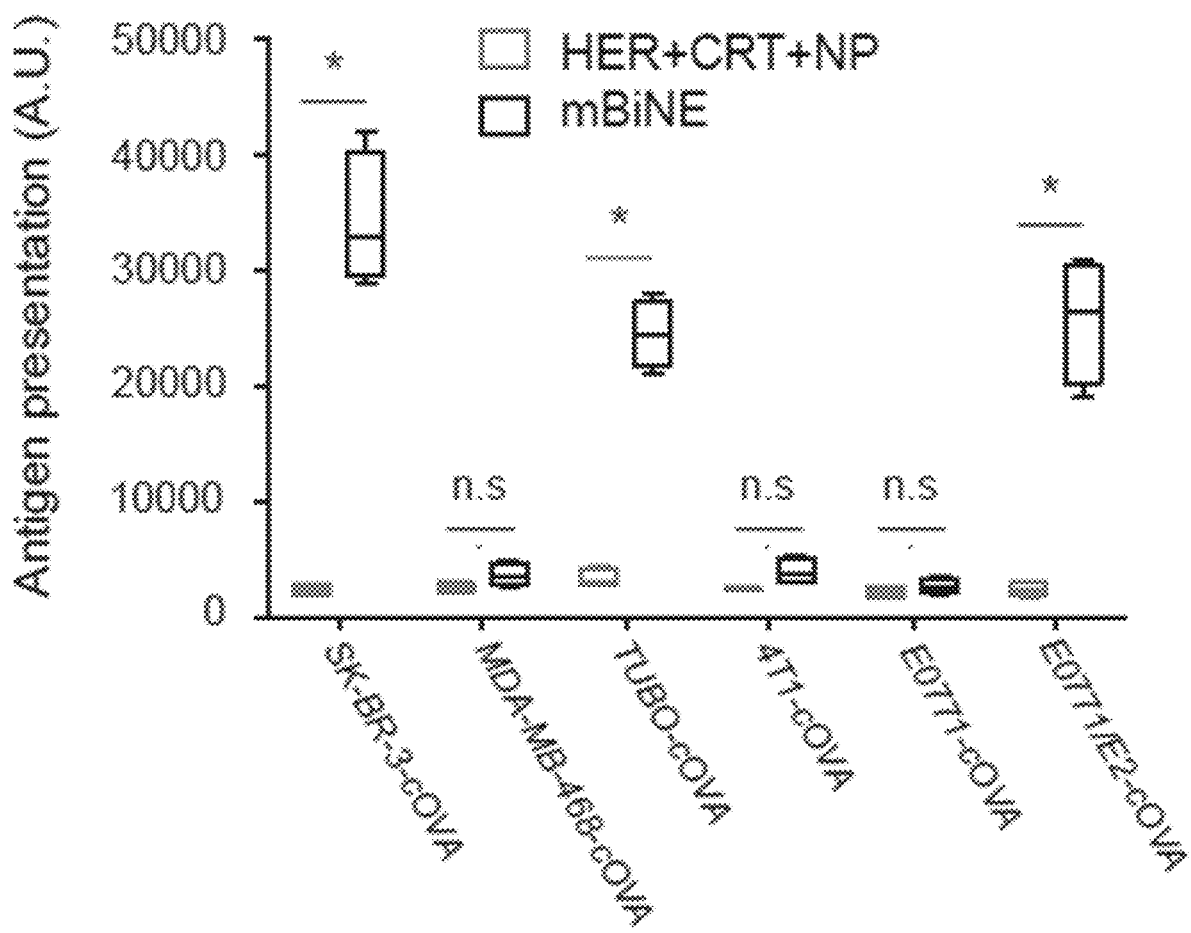
FIG. 8. Increased antigen presentation was only observed in cells over-expressing the HER2 receptor when treated with aHCNP as compared to unconjugated nanoparticles with Her2 antibodies and CRT.
Figure 9A:
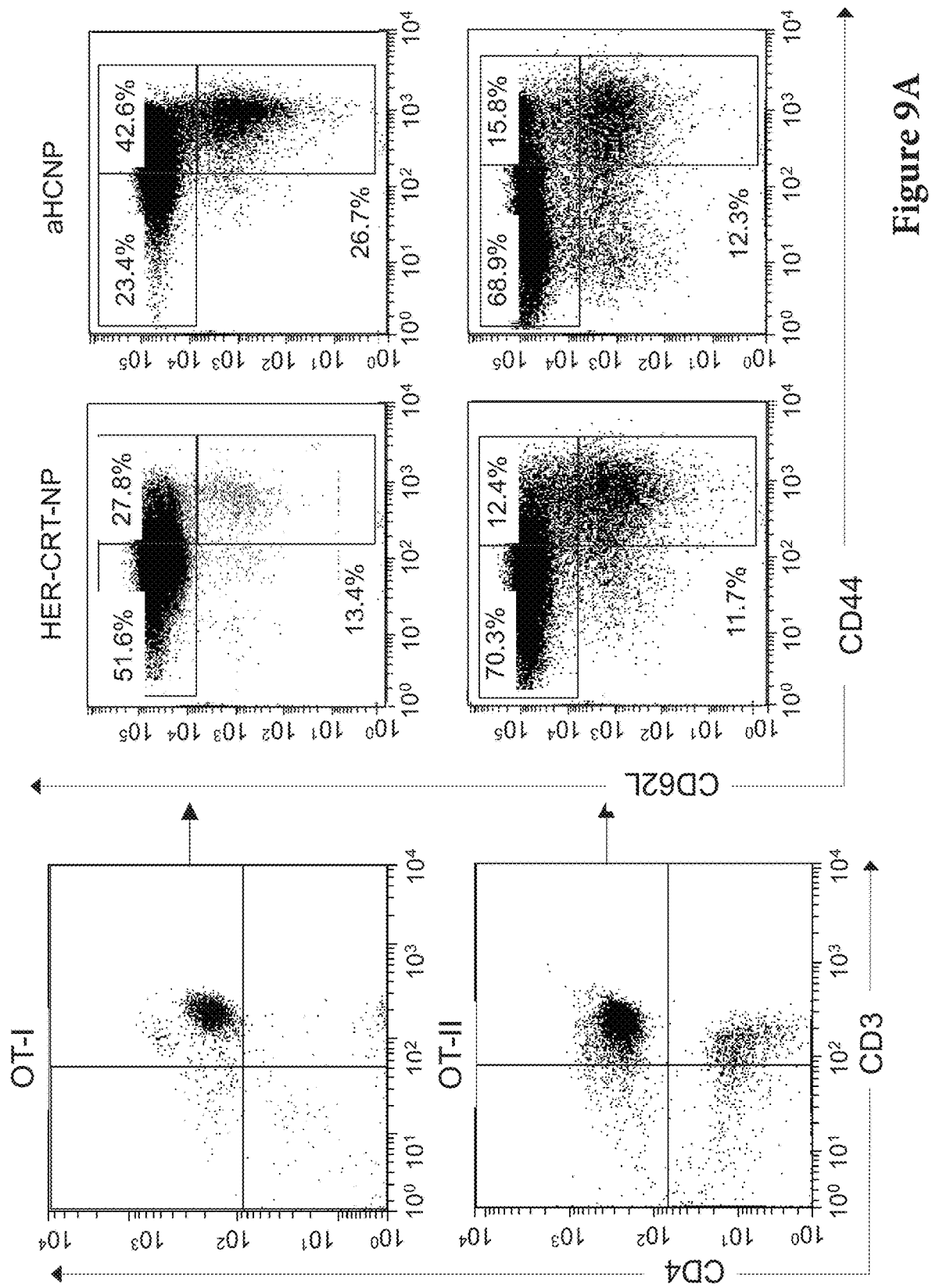
FIGS. 9A-9D. aHCNP primes a T cell response in vitro. a) CD3+/CD8+ and CD3+/CD4+ T cells were isolated from spleen of OTI and OTII mouse and purified with T cell isolation kit. CD3+/CD8+ and CD3+CD4+ T cells were then isolated using FACS and incubated with macrophages co-cultured with cOVA transfected EO771 and EO771/E2 breast cancer cells with or without aHCNP treatment. After 3 days of incubation, a significant increase in the activated CD8+ T cells based on CD44+/CD62Llow expression cells (activated T cells) and CD44+/CD62L+ expressing cells (memory T cells) were observed in the setting of aHCNP treatment compared to controls (a). There was a higher degree of CD8 T cell activation compared to CD4 T cells in aHCNP treatments (b-d). To test that the T-cell activation response is antigen specific, aHCNP treatments did not result in T cell activation in EO771 or EO771/E2 cells without cOVA transfection.
Figure 9B:
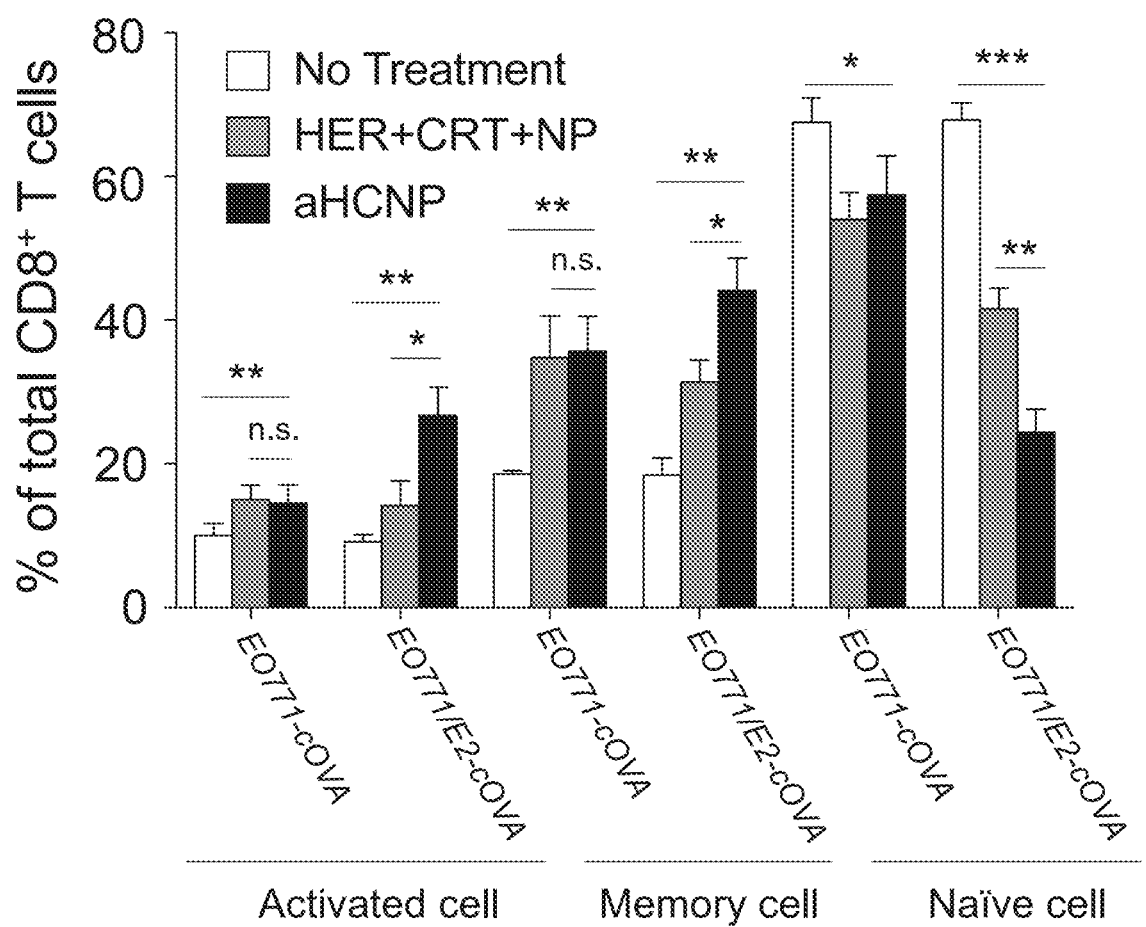
Figure 9C:
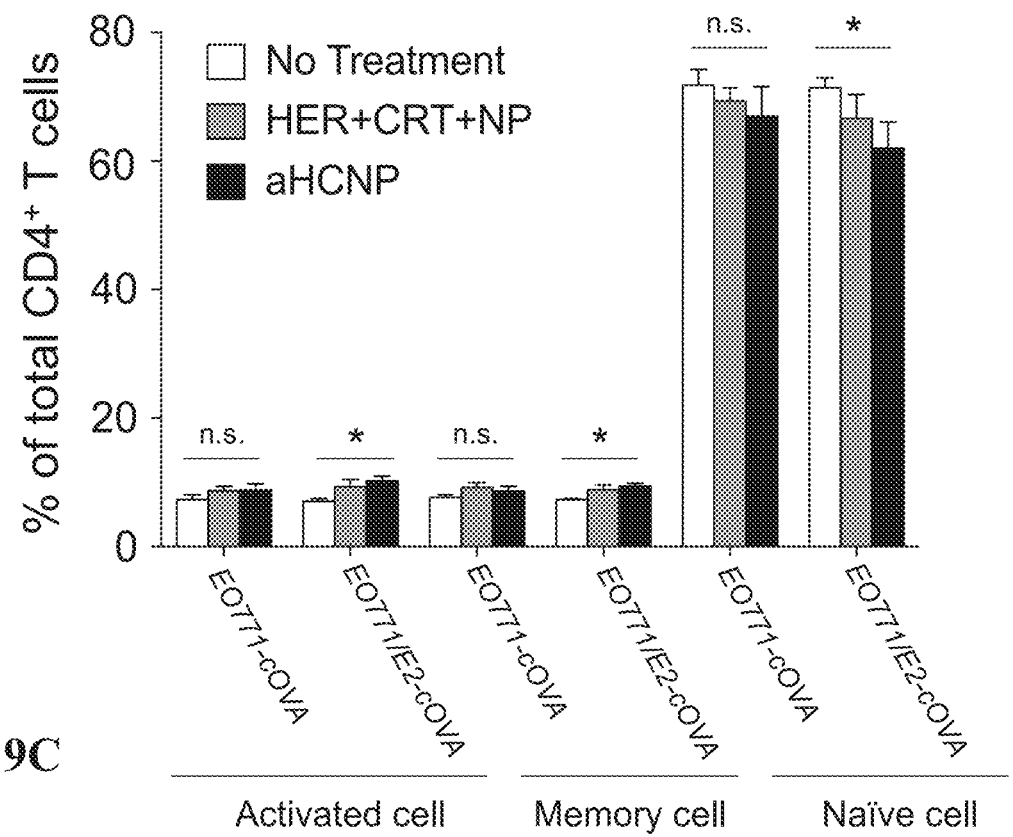
Figure 9D:
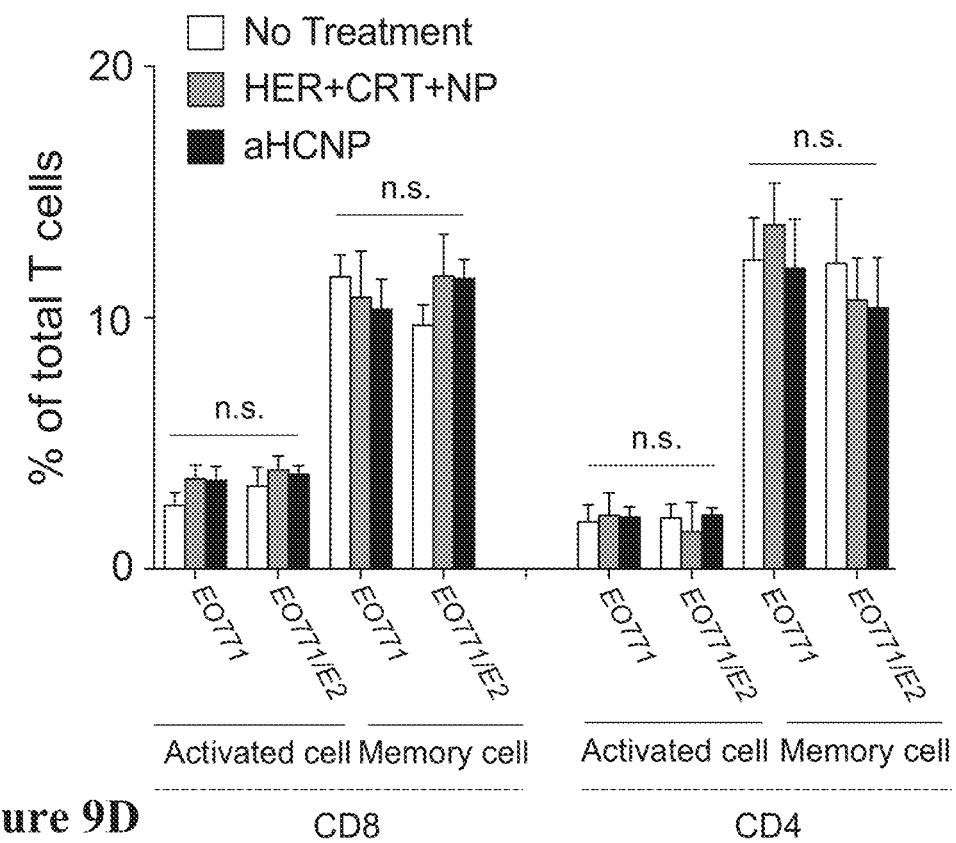

Nanoparticle Mediated Cancer Cell Phagocytosis Results in Increased Immune Activation The following was performed to demonstrate that the enhanced phagocytosis of HER2 over expressing cancer cells by macrophages mediated through a CRT pathway leads to down-stream immune processing and activation. The cancer cell lines were transfected with chicken ovalbumin (cOVA) and incubated with macrophages in the presence of nanoparticles conjugated with anti-CD340 antibodies and CRT polypeptides (aHCNP). The macrophages were then stained using an antibody that specifically labels MHC1 bound with cOVA derived peptide SIINFEKL. The macrophages demonstrated significantly higher antigen presentation for multiple human and mouse cell lines (FIG. 7). The enhanced presentation of cOVA derived peptide by the macrophage MHC1 was predominantly observed in HER2 over-expressing cell lines after treatment with nanoparticles conjugated with anti-CD340 antibodies and CRT polypeptides (aHCNP). Macrophages incubated with HER2 low-expressing MDA-MD-468 cells exhibited a much lower level of antigen presentation (FIG. 8), given that they had significantly lower phagocytosis activities towards these cells (FIG. 5).

The following was performed to determine whether the increases in target phagocytosis of cancer cells and subsequent enhanced antigen presentation can promote priming of T lymphocytes. After treatment with nanoparticles conjugated with anti-CD340 antibodies and CRT polypeptides (aHCNP), the macrophage were co-cultured with HER2 over-expressing, cOVA transfected E0771/E2 cells as well as the HER2 negative EO771 cells to determine if aHCNP is specific to HER2 over-expression tumors The macrophages were then co-cultured with both CD4 and CD8 T cells from OTII and OTI mice, respectively. E0771/E2 tumor cells treated with aHCNP resulted in significantly enhanced CD4 and CD8 T cell activation as compared to E0771 cells treated with aHCNP (FIGS. 9 and 23). No differences in tumour infiltrating T cell numbers were observed in E0771 tumours. Similarly, mBiNE-treated E0771/E2 tumors also demonstrated an increase in intratumoral macrophages, with minimal changes in the number of dendritic cells (FIG. 24).

A similar tumor growth inhibitory effect and immune activation status was observed with intravenously delivered mBiNE relative to intratumoral injections, although a higher dose level was needed to produce these effects (FIGS. 25-26). This observation confirmed the ability of mBiNE to elicit antitumor immune responses via either local or systemic routes, although different dosing regimens were needed to produce the optimal effects.

In light of mBiNE's ability to shift the CD8+ T-cell phenotype in HER2high tumour-bearing animals, it was determined whether the observed antitumour effect depends on host CD8+ T cells. Mice bearing E0771/E2 tumours were depleted of CD8+ T cells via intraperitoneal administration of anti-CD8 monoclonal antibodies (FIG. 27).

A similar effect also was observed in mice bearing TUBO tumours, suggesting that CD8+ T cells are involved in producing antitumour effects from mBiNE treatments (FIG. 28). It also was found that depletion of macrophages in E0771/E2 tumour-bearing mice by using anti-CSFR1 antibody significantly diminished the antitumour effect of mBiNE (FIGS. 29 and 30).

Taken together, the results provided herein demonstrate that the enhanced selective phagocytosis mediated by the nanoparticles provided herein (e.g., aHCNP) resulted in the activation of down-stream immune cascade that is also highly specific towards HER2 over expression tumor cells. This nanoparticle platform can be used to generate tumor-specific innate responses and subsequent tumor-specific adaptive immune system responses.

Given that CRT-mediated phagocytosis can promote antigen processing and immune activation of professional APCs, it was evaluated whether mBiNE treatment could enhance tumour antigen presentation in a receptor-targeted manner. Using a lentiviral vector to express cytoplasmic ovalbumin (cOVA), a well characterized immunogenic antigen, the following cell lines were transfected: human HER2high SK-BR-3 and HER2lowMDA-MB-468 cells; murine TUBO, a neu-overexpressing cell line derived from a spontaneous carcinoma in neu-transgenic mice; E0771/E2 cells, which express the human full-length HER2 protein; and HER2neg murine 4T1 and E0771 cells (FIG. 20).

Multivalent, Bi-Specific Nanoparticles Inhibit Tumor Growth and Generate Durable Anti-Tumor Immunity Using HER2 over-expressing syngeneic EO771/E2 and HER2 negative EO771 breast tumors, treatments with aHCNP significantly inhibited tumor growth in EO771/E2 tumors as compared to both PBS and unconjugated HER-CRT-NP controls. aHCNP treatments did not result in significant growth inhibition in HER2 negative EO771 tumors, suggesting the HER2 specific targeted eradication of cancer cells in vivo (FIGS. 10 and 21). Unconjugated HER-CRT-NP also had moderate levels of anti-tumor effects in EO771/E2 mice, due to the intrinsic anti-tumor ability of anti-Her2 antibodies and free CRT. Treatments with aHCNP also demonstrated immune activation effects as demonstrated by increased levels of systemic pro-inflammatory cytokines in the peripheral body, such as IL2 and IFNgamma (FIG. 11). When examining T cell activation in aHCNP treated and control animals, aHCNP treatments resulted in significantly elevated activation of CD8 T cells. The level of activated CD4 T cells remained stable, suggesting that cellular immunity mediated by CD8 T cells plays the predominant role in mediated the anti-tumor effects observed in aHCNP treated animals.

The ability of aHCNP to shift antigen-naïve CD8+ T cells towards the primarily less differentiated central memory phenotype further suggests the potential for generating durable and more potent antitumour immune responses. This conclusion was further supported by the observation that treatment with aHCNP (also referred to as a mBiNE) also increased tumor-specific IFN-γ production in CD8+ T cells, as determined by IFN-γ ELISPOT assay of purified CD8+ T cells from regional lymph nodes (FIG. 13A). Again, no significant T-cell responses with mBiNE treatments were observed in animals with HER2neg E0771 tumours (FIG. 11).

The observed therapeutic effect of mBiNE was further validated against TUBO tumours established in BALB/c mice as well as the poorly immunogenic MMTV-neu tumours in FVB mice (FIG. 22).

The following was performed to determine whether the treatment using aHCNP can generated immune memory against similar tumors. When initial implanted EO771/E2 tumors in the left mammary fat pad was treated with aHCNP, a second tumor was implanted in the mammary fat pad on the opposite side 2 weeks after the completion of treatment (FIG. 12). For the second tumor implantation, both HER2 overexpressing EO771/E2 and HER2 negative EO771 tumors were used. When the animals initially bearing the EO771/E2 tumors were treated with aHCNP, both EO771/E2 and EO771 tumors failed to engraft during the second tumor re-challenge (80% of the tumors failed to engraft). In contrast, PBS or unconjugated HER-CRT-NP treatments did not prevent second tumor engraftment. This result demonstrated that treatment with aHCNP can promote the generation of immune memory against related tumors. This immune memory produced by aHCNP treatment also is effective against tumor cells lacking the targeting receptor, which raise the notion that while HER2 receptor is involved in helping the immune system to recognize tumor cells by aHCNP initially, once the immune response is generated, it is potent against a wide range of tumor progenies. These results represent an advance in tumor immunotherapy, as it allows for receptor targeted immune eradication of cancer cells, as well as the generation of immunity against multiple clones of these cancer cells, including ones that have acquired mutations with altered expression or structural profiles of these receptors.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having cancer, said method comprising administering to said mammal a composition comprising particles, wherein said particles have a longest dimension of 1000 nm or less and comprise (a) an anti-cancer antigen antibody and (b) calreticulin, wherein incubation of cancer cells and said antigen presenting cells in the presence of said composition results in increased phagocytosis of said cancer cells by said antigen presenting cells as compared to the level of phagocytosis of comparable cancer cells by comparable antigen presenting cells in the absence of said composition,
   wherein said anti-cancer antigen antibody is conjugated to a surface of said particles,
   wherein said calreticulin is conjugated to a surface of said particles, and
   wherein said anticancer antigen antibody is an anti-CD340 antibody, an anti-EGFR antibody, an anti-PSMA antibody, an anti-EGFRviii antibody, an anti-CEA antibody, an anti-CA125 antibody, an anti-CD20 antibody, an anti-CD30 antibody, an anti-CD33 antibody, or an anti-GD antibody.

2. The method of claim 1, wherein said mammal is a human.

3. The method of claim 1, wherein said cancer is breast cancer, brain cancer, prostate cancer, lung cancer, or colorectal cancer.

4. The method of claim 1, wherein said composition is administered by injection, ingestion, or inhalation.

* * * * *